United States Patent [19]
Hsueh et al.

[11] Patent Number: 5,925,549
[45] Date of Patent: Jul. 20, 1999

[54] SOLUBLE 7-TRANSMEMBRANE DOMAIN G-PROTEIN-COUPLED RECEPTOR COMPOSITIONS AND METHODS

[75] Inventors: Aaron J. W. Hsueh, Stanford; Brian K. Kobilka, Palo Alto; Masataka Kudo, Menlo Park, all of Calif.

[73] Assignee: The Board of Trustees of the Leland Stanford Junior University, Stanford, Calif.

[21] Appl. No.: 08/837,151

[22] Filed: Apr. 14, 1997

Related U.S. Application Data

[60] Provisional application No. 60/015,450, Apr. 15, 1996.
[51] Int. Cl.$^6$ .................. C07K 14/705; C07K 16/28; C12N 15/62
[52] U.S. Cl. ............... 435/69.7; 435/69.1; 435/252.3; 435/320.1; 530/350; 536/23.4
[58] Field of Search ........................ 435/69.1, 69.7, 435/252.3, 320.1; 536/23.4; 530/350

[56] References Cited

U.S. PATENT DOCUMENTS

| | | | |
|---|---|---|---|
| 5,359,046 | 10/1994 | Capon et al. | 536/23.4 |
| 5,447,851 | 9/1995 | Beutler et al. | 435/69.7 |
| 5,494,806 | 2/1996 | Segre et al. | 435/69.1 |

FOREIGN PATENT DOCUMENTS

| | | |
|---|---|---|
| 0 471 030 B1 | 12/1994 | European Pat. Off. . |
| WO 92/16620 | 10/1992 | WIPO . |
| WO 92/22667 | 12/1992 | WIPO . |
| WO 95/22340 | 8/1995 | WIPO . |
| WO 96/38575 | 12/1996 | WIPO . |

OTHER PUBLICATIONS

Benkirane, M. et al., "The cytoplasmic domain of CD4 plays a critical role during the early stages of HIV infection in T–cells," The EMBO Journal 13(23):5559–5569 (1994).
Jelinek, L.J., et al., "Expression Cloning and Signaling Properties of the Rat Glucagon Receptor," Science 259:1614–1616 (1993).
Lin, C. et al., "Pit–1–dependent expression of the receptor for growth hormone releasing factor mediates pituitary cell growth," Nature 360:756–768 (1992).
Masu, M. et al., "Sequence and expression of a metabotropic glutamate receptor," Nature 349: 760–765 (1991).
Thorens, B. et al., "Cloning and Functional Expression of the Human Islet GLP–1 Receptor," Diabetes 42: 1678–1682 (1993).
Chen, W. and Bahl, O.P. (1993) "High Expression of the Hormone Binding Active Extracellular Domain (1–294) of Rat Lutropin Receptor in *Escherichia coli*", *Molecular and Cellular Endocrinology*, 91:35–41.
Chen, J. et al. (1994) "Confirmation of the Intramolecular Tethered Liganding Hypothesis and Discovery of an Alternative Intermolecular Liganding Mode", *The Journal of Biological Chemistry*, 269(23):16041–16045.
Deng, H. et al. (1996) "Identification of a Major Co–Receptor for Primary Isolates of HIV–1", *Nature*, 381:661–666.
Feng, Y. et al. (1996) "HIV–1 Entry Cofactor: Functional cDNA Cloning of a Seven–Transmembrane, G Protein–Coupled Receptor", *Science*, 272:872–877.
Ji, I. and Ji, T.H. (1991) "Exons 1–10 of the Rat LH Receptor Encode a High Affinity Hormone Binding Site and Exon 11 Encodes G–Protein Modulation and a Potential Second Hormone Binding Site", *Endocrinology*, 128(5):2648–2650.
Ji, I. and Ji, T.H. (1991) "Human Choriogonadotropin Binds to a Lutropin Receptor With Essentially No N–Terminal Extension and Stimulates cAMP Synthesis", *The Journal of Biological Chemistry*, 266(20):13076–13079.
Loosfelt, H. et al. (1989) "Cloning and Sequencing of Porcine LH–hCG Receptor cDNA: Variants Lacking Transmembrane Domain ", *Science*, 245:525–528.
McFarland, K.C. et al. (1989) "Lutropin–Choriogonadotropin Receptor : An Unusual Member of the G Protein–Coupled Receptor Family", *Science*, 245:494–499.
Tsai–Morris, C.H. et al. (1990) "Intronic Nature of the Rat Luteinizing Hormone Receptor Gene Defines a Soluble Receptor Subspecies with Hormone Binding Activity", *The Journal of Biological Chemistry*, 265(32):19385–19388.
Tsai–Morris, C.H. et al. (1991) "Structural Organization of the Rat Luteinizing Hormone (LH) Receptor Gene", *The Journal of Biological Chemistry*, 266(17):11355–11359.
VuHai–LuuThi, M.T. et al. (1992) "Variant Forms of the Pig Lutropin/Choriogonadotropin Receptor", *Biochemistry*, 31:8377–8383.
Braun, T., et al., "Amino–Terminal Leucine–Rich Repeats in Gonadotropin Receptors Determine Hormone Selectivity," *EMBO Journal*. 10(7):1885–1890 (1991).
Ji, I. and Ji, T.H., "Differential Roles of Exoloop 1 of the Human Follicle–stimulating Hormone Receptor in Hormone Binding and Receptor Activation," *Journal of Biological Chemistry*. 270(27):15970–15973 (1995).
Thomas, D.M. and Segaloff, D.L., "Hormone–Binding Properties and Glycosylation Pattern of a Recombinant Form of the Extracellular Domain of the Luteinizing Hormone/Chorionic Gonadotropin Receptor Expressed in Mammalian Cells," *Endocrinology*. 135(5):1902–1912 (1994).
Vilardaga, J.–P., "Properties of Chimeric Secretin and VIP Receptor Proteins indicate the Importance of the N–Terminal Domain for Ligand Discrimination," *Biochemical and Biophysical Research Communications*. 211(3):885–891 (1995).
Xie, Y.–B., et al., "Extracellular Domain of Lutropin/Choriogonadotropin Receptor Expressed in Transfected Cells Binds Choriogonadotropin with High Affinity," *Journal of Biological Chemistry*. 265(35):21411–21414 (1990).

*Primary Examiner*—John Ulm
*Attorney, Agent, or Firm*—Charles K. Sholtz; Joanne R. Petithory; Dehlinger & Associates

[57] ABSTRACT

Chimeric polypeptides containing the N-terminal amino acid sequence of a glycoprotein hormone receptor polypeptide and a membrane anchor polypeptide, with a protease recognition site between the two, are disclosed. Also disclosed are nucleic acids encoding such polypeptides, expression vectors containing such nucleic acids and methods of producing such recombinant chimeric polypeptides, as well as uses thereof. The chimeric polypeptides are particularly useful for the production of soluble glycoprotein hormone receptor polypeptides.

37 Claims, 8 Drawing Sheets

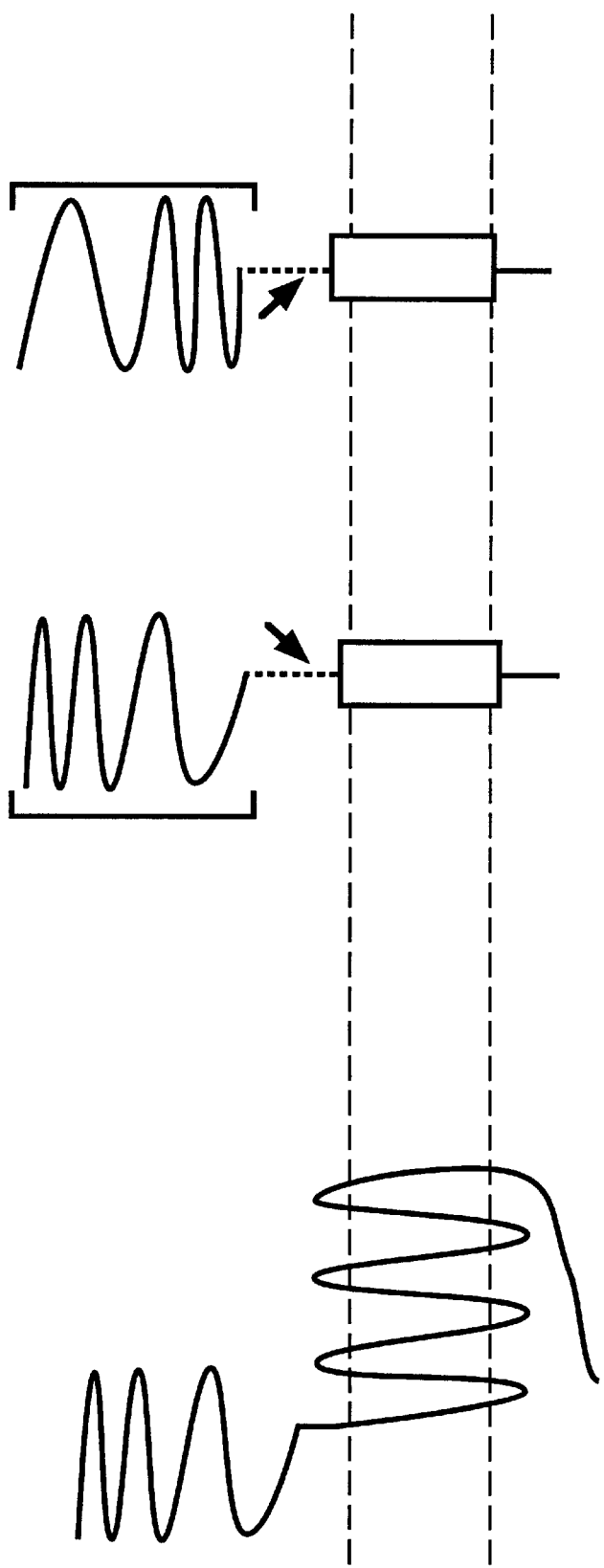

SOLUBLE 7-TRANSMEMBRANE DOMAIN G-PROTEIN-COUPLED RECEPTOR COMPOSITIONS AND METHODS

This application claims priority under 35 USC 120 to Provisional U.S. patent application Ser. No. 60/015,450, filed Apr. 15, 1996, herein incorporated by reference.

This work was supported in part by National Institutes of Health Grant HD-23273. Accordingly, the United States Government has certain rights in this invention.

FIELD OF THE INVENTION

The present invention relates in general to fusion proteins comprising a membrane anchor and the extracellular ligand binding domain of a 7-transmembrane domain G-protein-coupled receptor. More specifically, the invention relates to fusion proteins containing the extracellular ligand binding domains of glycoprotein hormone receptors, methods of efficiently producing such soluble glycoprotein hormone receptors, and uses thereof.

REFERENCES

Abe, T., et al., *J. Biol. Chem.* 267:13361 (1992).

Abou-Samra, A. -B., et al., *Proc. National Acad. Sci. USA* 89:2732 (1992).

Ausubel, F. M., et al., *CURRENT PROTOCOLS IN MOLECULAR BIOLOGY*, John Wiley and Sons, Inc., Media, PA (1988).

Banga, A. K., *THERAPEUTIC PEPTIDES AND PROTEINS FORMULATION, PROCESSING AND DELIVERY SYSTEMS*, Technomic Publishing Co., Inc., Lancaster, Pa. (1995).

Billig, H., et al., *Endocrinology* 136:5–12 (1995).

Bobovnikova, et al., *Endocrinol.* 138:588 (1997).

Bozon, et al., *J. Mol. Endo.* 14:277 (1995).

Brain and Cambridge, *General Pharmacol.* 27:607 (1996).

Bunin, B. A., et al., *Proc. Natl. Acad. Sci. USA* 91:4708 (1994).

Chazenbalk and Rapoport, *J. Biol. Chem.* 270:1543 (1995).

Chen, J., et al., *J. Biol. Chem.* 269(23):16041–16045 (1994).

Chen, W., and Bahl, O. P., *Mol. & Cell. Endocrinol.* 91:35–41 (1993).

Chiauzzi, V., et al., *J. Clin. Endocrinol. Metab.* 54:1221–8 (1982).

Cwirla, S. E., et al., *Proc. Natl. Acad. Sci. U.S.A.* 87:6378 (1990).

Davoren, J. B., and Hsueh, A. J. W., *Biol. Reprod.* 33:37–52 (1985).

Decker, G. H., et al., *J. Steroid Biochem. Mol. Biol.* 42:705–12 (1992).

Dennis, T., et al., *J. Pharmacol. Ther.* 251:718–725 (1989a).

Dennis, T., et al., *J. Pharmacol. Ther.* 254:123–128 (1989b).

Devlin, J. J., et al., *Science* 249:404 (1990).

Dias, J. A., et al., *Fertil. Steril.* 38:330–8 (1982).

Epand, R. M., and Caulfield, M. P., "Calcitonin and Parathyroid Hormone Receptors" In *COMPREHENSIVE MEDICINAL CHEMISTRY. VOL. 3 (MEMBRANES AND RECEPTORS)*, Hansch, C., et al., Eds., Pergamon Press, Oxford, pp. 1023–1045 (1990).

Fauser, B. C., *Mol. Hum. Reprod.* 2: 327–334 (1996).

Feng, Y., et al., *Science* 272:872 (1996).

Feuerstein, G., et al., *Canadian J. Physiol. and Pharmacol.* 73:1070 (1995).

Fong, T. M., et al., *Nature* 362:350–353 (1993).

Gearing, D. P., et al., *Bio/Technology* 7:1157–1161 (1989).

Gennaro, A. R., Ed., *REMINGTON'S PHARMACEUTICAL SCIENCES* (18th ed., Mack, Easton Pa. (1990)).

Goke, R., et al., *Eur. J. Invest.* 21:135–144 (1991).

Harlow, E., et al., in *ANTIBODIES: A LABORATORY MANUAL*, Cold Spring Harbor Laboratory Press (1988).

Hill and Wallick, *Am. J. Physiol.* 38:H1467 (1995).

Houghten, R. A., *Proc. Natl. Acad. Sci. USA* 85:5131–5135 (1985).

Houghten, R. A., *Current Biology* 4:564 (1994).

Houghten, R. A., et al., *BioTechniques* 4:522–528 (1986).

Houghten, R. A., et al., *Nature* 354:84–86 (1991).

Houghten, R. A., et al., *BioTechniques* 13:412–421 (1992).

Indridason, O., et al., *Kidney International* 50:1663 (1996).

Ishihara, T., et al., *EMBO J.* 10:1635–1641 (1991).

Ishihara, T., et al., *Neuron* 8:811–819 (1992).

Jelinek, L. J., et al., *Science* 259:1614 (1993).

Jia, X. C., et al., *Mol. Endocrinol.* 5:759–768 (1991).

Juppner, H., et al., *Science* 254:1024–6 (1991).

Kudo, M., et al., *J. Biol. Chem.* 271:22470–22478 (1996).

Lin, H. Y., et al., *Science* 254:1022–4 (1991).

Littman, et al., *Cell* 40:237–246 (1985).

Magner, J. A., *Endocrin. Per.* 11:354 (1990).

Masu, M., et al., *Nature* 349:760 (1991).

Mayo, K. E., *Mol. Endocrinol.* 6:1734–1744 (1992).

McFarland, K. C., et al., *Science* 245:494–499 (1989).

Muff, R., et al., *Annul Rev. Physiol.* 54:67–81 (1992).

Mullis, K. B., et al., U.S. Pat. No. 4,683,195, issued Jul. 28, 1987.

Mullis, K. B., U.S. Pat. No. 4,683,202, issued Jul. 28, 1987.

Nagayama, Y., and Rapoport, B., *Mol. Endocrinol.* 6:145–156 (1992).

Nielsen P., et al., *J. Clin. Endo. Metab.* 81:3793 (1996).

Pajot-Augy, et al., *J. Mol. Endo.* 14:51 (1995).

Petersdorf, R. G., et al., (Eds.), In: *HARRISON'S PRINCIPLES OF INTERNAL MEDICINE. 10TH ED.* McGraw-Hill, NY, pp 710 (1983).

Reichert, L. E., et al., *Trends Pharmacol. Sci.* 12:199–203 (1991).

Said, S. I. and Mutt, V. (eds) *VASOACTIVE INTESTINAL POLYPEPTIDE AND RELATED PEPTIDES. Ann. N.Y. Acad. Sci.* 527 (1988).

Scatchard, G., *Ann. N.Y. Acad. Sci.* 51:660–666 (1949).

Schoepp, D. D. and Conn, P. J., *Trends Pharmacol. Sci.* 14:13–20 (1993).

Scott, J. K., and Smith, G. P., *Science* 249:386 (1990).

Seetharamaith, G. S., et al., *Endocrinol.* 134:549 (1994).

Smith, D. B. and Johnson, K. S., *Gene* 67:31–40 (1988).

Takahashi, K., et al., *J. Biol. Chem.* 268:19341–5 (1993)

Tanabe, Y., et al., *Neuron* 8:169 (1992).

Tanchristensen, M., et al., *Am. J. Physiol.* 40:R848 (1996).

Tapanainen, J. S., et al., *Mol. Endocrinol.* 7:643–650 (1993).

Thiele, T. E., et al., *Am. J. Physiol.* 41:R726 (1997).

Thorell, J., and Johansson, B., *Biochim. Biophys. Acta* 251:363 (1971).

Thorens, B., *Proc. National Acad. Sci. USA* 89:8641 (1992).

Tilly, J. L., et al., *Endocrinology* 131:799–806 (1992).

Tomer, T., and Davies, T. F., *Endocrine Rev.* 14:107–120 (1993).

Tsai-Morris, C. H., et al., *J. Biol. Chem.* 265:19385–88 (1990).

Vantine, B., et al., *Endocrinol.* 137:3316 (1996).

Virgilio, A. A., and Ellman, J. A., *J. Am. Chem. Soc.* 116:11580 (1994).

Vu, T. K., et al., *Cell* 64:1057–68 (1991).

Watson, S. and Arkinstall, S., *THE G-PROTEIN LINKED RECEPTOR FACTSBOOK*, Academic Press, New York (1994).

Wilmen, A., et al., *FEBS letters* 398:43 1996.

Wrighton, N. C., et al., *Science* 273:458–463 (1996).

Xie, Y. B., et al., *J. Biol. Chem.* 265:21411–20 (1990).

BACKGROUND OF THE INVENTION

Glycoprotein hormone receptors (GhRs) are a family of receptors for glycoprotein hormones secreted by the anterior pituitary. These hormones include the gonadotropins, such as luteinizing hormone (LH; lutropin), and follicle stimulating hormone (FSH; fillitropin), as well as thyroid stimulating hormone (TSH; thyrotropin), and choriogonadotropin (CG), which is produced by the placenta. Each hormone selectively binds to a member of the GhR family—LH and human CG (hCG) bind to the LH receptor (LHR), FSH binds to the FSH receptor (FSHR), and TSH binds to the TSH receptor (TSHR). The biological consequences of ligand binding to a GhR, typically mediated by an increase in the intracellular concentration of cAMP, result in steroid synthesis and secretion, as well as target cell activation and differentiation.

Situations exists where it would be desirable to efficiently express only the ligand binding portion of a selected GhR. However, past attempts to achieve such expression have been unreproducible or have resulted at best in inefficient and/or unpredictable levels of expression (Xie, et al., 1990; Tsai-Morris, et al., 1990). For example, although full length human FSH, LH and TSH receptors have been successfully expressed using the baculovirus expression system, expression of the extracellular region of both porcine LH receptor and human TSH receptor resulted in the trapping of this domain inside the host cells (Pajot-Augy, et al., 1995; Seetharamaith, et al., 1994; Chazenbalk and Rapoport, 1995). While ligand binding could be observed, the vast majority of the proteins were in a denatured, inactive and unprocessed form.

In one recent study (Bozon, et al., 1995), moderate amounts (100,000 sites/cell) of porcine LH receptor extracellular region were secreted into the media if a low expression promoter/signal peptide combination was used. However, because high expression levels invariably led to intracellular protein aggregation, it was concluded that only a moderate level of expression is compatible with production of bioactive ectodomain of the receptor. The authors (Bozon, et al., 1995) proposed to perform immunoaffinity purification of the recombinant proteins and to refold aggregated receptors using guanidine HCl in the presence of cystine and cysteine, as was done for the TSH receptor (Bobovnikova, et al., 1997).

In *E. Coli,* expression of the extracellular region of rat LH receptor also led to the production of self-associated protein aggregates in the inclusion bodies (Chen and Bahl, 1993). While the proteins could be refolded, the re-folding process was inefficient and difficult to do consistently, perhaps because proteins derived from prokaryotic cells lack carbohydrate side chains that are necessary to facilitate proper protein folding.

The present invention provides a convenient method, not encumbered by the above-described difficulties, for efficiently and reliably expressing such "soluble glycoprotein hormone receptors" (sGhRs). The method may also be applied to the expression of the extracellular ligand binding domains of other 7-transmembrane domain G-protein-coupled receptors having the substantial majority of their ligand binding activity in the extracellular portion of the receptor. Summary of the Invention In one aspect, the present invention includes a chimeric nucleic acid molecule formed of a 5' end segment that encodes an extracellular ligand binding region (ELBR) of a 7-transmembrane domain G-protein-coupled receptor polypeptide, a 3' end segment that encodes a membrane anchor polypeptide, and interposed between the 5' end segment and 3' end segment, a protease recognition site.

In one embodiment, the 7-transmembrane domain G-protein-coupled receptor polypeptide is a calcitonin receptor. In a related embodiment, the 7-transmembrane domain G-protein-coupled receptor polypeptide is a calcitonin-gene related peptide (CGRP) receptor. In another embodiment, the 7-transmembrane domain G-protein-coupled receptor polypeptide is a glucagon receptor. In a related embodiment, the 7-transmembrane domain G-protein-coupled receptor polypeptide is a glucagon-like peptide 1 (GLP-1) receptor. In still another embodiment, the 7-transmembrane domain G-protein-coupled receptor polypeptide is a metabotropic glutamate receptor. In another embodiment, the 7-transmembrane domain G-protein-coupled receptor polypeptide is a parathyroid hormone (PTH) receptor. In yet another embodiment, the 7-transmembrane domain G-protein-coupled receptor polypeptide is a vasoactive intestinal peptide (VIP) receptor. In still another embodiment, the 7-transmembrane domain G-protein-coupled receptor polypeptide is a secretin receptor. In an additional embodiment, the 7-transmembrane domain G-protein-coupled receptor polypeptide is a growth hormone releasing factor (GRF) receptor.

In a general embodiment, the protease recognition site is a thrombin recognition site. In another general embodiment, the 3' end segment encodes the transmembrane portion of a CD8 molecule.

In a preferred general embodiment, the 7-transmembrane domain G-protein-coupled receptor polypeptide is a glycoprotein hormone receptor. In another preferred general embodiment, the 3' and 5' end segments are heterologous with respect to one another.

In one embodiment, the 5' end segment encodes a human luteinizing hormone receptor binding protein (LBP). In another embodiment, the 5' end segment encodes a human follicle stimulating hormone receptor binding protein (FBP). In still another embodiment, the 5' end segment encodes a human thyroid stimulating hormone receptor binding protein (TBP).

Also included in the invention is an expression vector comprising (a) a chimeric nucleic acid molecule such as described above, and (b) regulatory sequences effective to express an open reading frame of the chimeric nucleic acid molecule in a host cell.

In another aspect, the invention includes a method of recombinantly producing a fusion polypeptide encoded by the chimeric nucleic acid molecule described above. The method includes the steps of (i) introducing into suitable host cells, the above-described expression vector, and (ii) culturing the host cells under conditions resulting in the expression of the fusion polypeptide. In a general embodiment, the method further includes incubating the host cells in the presence of a protease which recognizes the protease recognition site, to release the first segment of the chimeric polypeptide.

Also included in the invention are host cells transfected with an expression vector such as described above.

In another aspect, the invention includes a chimeric polypeptide formed of a first segment that contains an extracellular ligand binding region (ELBR) of a 7-transmembrane domain G-protein-coupled receptor polypeptide, a second segment that contains a membrane anchor polypeptide, and interposed between the first and second segments, a protease recognition site. In specific embodiments, the segments can include the corresponding polypeptide entities encoded by the above-described chimeric nucleic acid molecules. In a preferred embodiment, the first and second segments are heterologous with respect to one another.

The 7-transmembrane domain G-protein-coupled receptor polypeptide may be, for example, a calcitonin receptor, a calcitonin-gene related peptide (CGRP) receptor, a glucagon receptor, a glucagon-like peptide 1 (GLP-1) receptor, a metabotropic glutamate receptor, a parathyroid hormone (PTH) receptor, a vasoactive intestinal peptide (VIP) receptor, a secretin receptor, or a growth hormone releasing factor (GRF) receptor. In a preferred general embodiment, the 7-transmembrane domain G-protein-coupled receptor polypeptide is a glycoprotein hormone receptor.

These and other objects and features of the invention will become more fully apparent when the following detailed description is read in conjunction with the accompanying drawings.

BRIEF DESCRIPTION OF THE FIGURES

FIGS. 1A, 1B and 1C are diagrams of wild type (FIG. 1A) and anchored receptors, FtCD8 (FIG. 1B) and LtCD8 (FIG. 1C). The arrowheads in FIGS. 1B and 1C indicate the general location of the protease recognition sites. Extracellular portions of the receptors schematized in FIGS. 1B and 1C are indicated by square brackets.

DETAILED DESCRIPTION OF THE INVENTION

I. Definitions

Figure 2A:
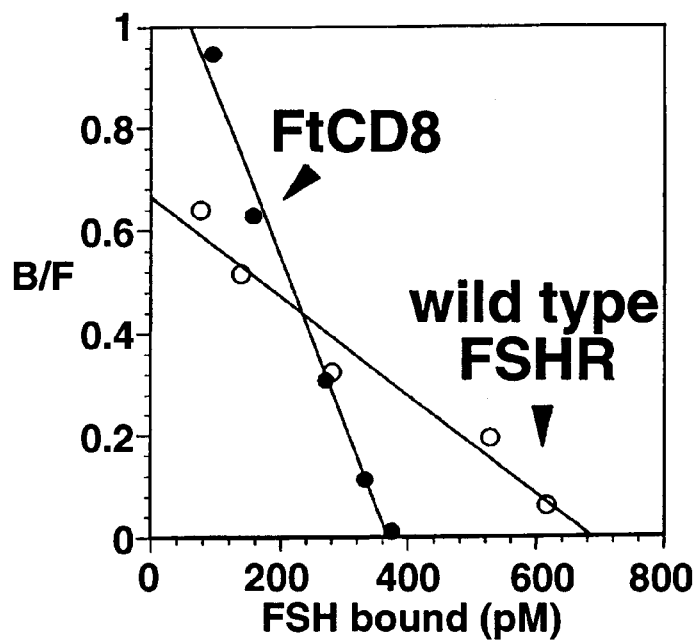
FIG. 2A is a plot of the binding kinetics of wild type FSH receptor and FtCD8.

A first polynucleotide fragment or polypeptide fragment is said to "correspond to" a second polynucleotide fragment or polypeptide fragment, respectively, when the fragments or regions are essentially co-extensive with one another when sequences representing the fragments are aligned using a sequence alignment program, such as "MACVECTOR" (IBI, New Haven, Conn.). "Corresponding" polynucleotide or polypeptide fragments typically contain a similar, if not identical, number of residues. It will be understood, however, that corresponding fragments may contain insertions or deletions of residues with respect to one another, as well as some differences in their sequences.

A polypeptide sequence or fragment is "derived from" another polypeptide sequence or fragment when it contains the same or substantially the same sequence of amino acids as are present in the sequence or fragment from which it is derived. For example, an SED is "derived from" a particular 7-transmembrane domain G-protein-coupled receptor (e.g., TSH receptor) when it has an amino acid sequence which is the same or substantially the same as the sequence of the corresponding region from the extracellular domain of that receptor.

The term "soluble extracellular domain" (SED) refers to a polypeptide containing all or a part of the extracellular portion of a 7-transmembrane domain G-protein-coupled receptor, said part containing a sequence of at least about 10, preferably at least about 15, more preferably at least about 20 consecutive amino acids derived from said portion.

The term "soluble glycoprotein hormone receptor" (sGhR) refers to an SED derived from a glycoprotein hormone receptor, such as an LH, FSH or TSH receptor, where the SED has ligand binding properties that are within about an order of magnitude of those associated with the intact receptor.

The term "soluble binding protein" (sBP), refers to a polypeptide containing the extracellular portion of a 7-transmembrane domain G-protein-coupled receptor, where the polypeptide has ligand binding properties that are within about an order of magnitude of those associated with the intact receptor.

The term "soluble glycoprotein hormone binding protein" (sGhBP), refers to a polypeptide containing the extracellular portion of a glycoprotein hormone receptor, such as an LH, FSH or TSH receptor, where the polypeptide has ligand binding properties that are within about an order of magnitude of those associated with the intact receptor. Examples of sGhBP's are LBP (contains the extracellular portion of the LH receptor), FBP (contains the extracellular portion of the FSH receptor), and TBP (contains the extracellular portion of the TSH receptor).

The terms "extracellular ligand binding region" (ELBR) and "solubilized ligand binding region" (SLBR) refer to an SED that has ligand binding properties that are within about an order of magnitude of those associated with the intact receptor.

It will be understood that an sGhBP, ELBR or SLBR may be modified or mutated relative to the corresponding native fragment so that the binding kinetics or affinity of the modified sGhBP, ELBR or SLBR for the ligand are substantially greater or less than those of the native receptor. Applications for such modified sGhBPs, ELBRs and SLBRs are discussed below.

The term "soluble antigenic domain" refers to an SED that is specifically immunoreactive with antibodies that are specifically immunoreactive with or generated against (i) the intact selected receptor or (ii) the complete extracellular domain of the selected receptor.

Two polynucleotide or polypeptide fragments are said to be "heterologous with respect to one another" when the sequence of each fragment is derived from a different gene. For example, a fragment derived from a TSH receptor is heterologous to a fragment derived from a CD8 molecule.

An antibody or antibody composition (e.g., polyclonal antibodies) is "specifically immunoreactive" or "selectively immunoreactive" with a particular antigen (e.g., the extracellular domain of a TSH receptor) when the antibody or antibody composition is immunoreactive with that antigen but not with antigens present in other 7-transmembrane domain G-protein-coupled receptors.

The terms "substantially purified" and "substantially-isolated", when used to describe a polynucleotide, polypeptide or antibody composition, refer to compositions or preparations which are substantially free of materials with which these products are normally and naturally found.

The term "significant", when used with reference to "significantly different", "significantly inhibits" or "significantly stimulates", refers to a difference in a quantifiable parameter between the two groups being compared that is statistically-significant using standard statistical tests. For example, the degree of binding in a protein binding assay may be quantified using standard methods, and the degree of binding under different conditions can be compared for statistically-significant differences.

"Treating" a disease or condition refers to an action which results in a lessening of the severity of symptoms of the disease and/or an inhibition of the pathogen or pathological process underlying the disease.

II. 7-Transmembrane Domain G-Protein-Coupled Receptors

The present invention relates to the soluble extracellular domains of a subset of receptors belonging to the 7-transmembrane domain G-protein-coupled receptor (7-TDGR) superfamily, and to the efficient production or expression of such ligand-binding domains.

Receptors belonging to the 7-TDGR superfamily are transmembrane proteins present in the plasma membrane and characterized by amino acid sequences which contain seven hydrophobic domains predicted to form the membrane-spanning regions. They transmit extracellular stimuli to the interior of the cell via interactions with heterodimeric G-proteins. The stimuli for different receptors in the superfamily include light, taste, odor, small peptides, amino acid derivatives and lipid analogs (see, e.g., Watson and Arkinstall, 1994). In many members of the 7-TDGR superfamily, including the subset of receptors to which the present invention applies, activation of the receptor results in stimulation of Gs, the stimulatory subunit of G-protein, which in turn activates adenylyl cyclase, causing a rise in intracellular cAMP.

The general belief in the art had been that the ligand binding sites of 7-TDGRs with short N-terminal extracellular regions were contained mainly in the transmembrane regions of the receptors. It has been discovered, however, that for certain types of 7-TDGR (the subset to which the present invention applies), the extracellular portion has, in the absence of transmembrane domains, ligand binding activity comparable to that of the intact receptor, i.e., the affinity of the ligand for the extracellular portion is within about an order of magnitude of its affinity for the intact receptor. This phenomenon is illustrated herein by experiments showing that the extracellular portion of a glycoprotein hormone G-protein-coupled receptor can bind to its corresponding signalling molecule in the absence of the transmembrane and intracellular domains, with an affinity similar to that observed in an intact, native receptor.

Due to the high degree of homology in the 7-transmembrane domains of the receptors, identification of novel members of this superfamily, as well identification of the extracellular portions of such novel members, is readily accomplished by those of skill in the art. By way of example, the book of Watson and Arkinstall (1994), incorporated herein by reference, provides the sequences of over 50 members of the 7-transmembrane domain G-protein-coupled receptor superfamily. The book further describes, for each sequence, the precise residues comprising the transmembrane domains. The "extracellular portions" of these receptors (as well as other 7-TDGRs) are the regions between the N-termini and the start of the first transmembrane domains (indicated as "TM 1").

III. Overview of the Invention

Experiments detailed herein demonstrate that stable high-level expression of the extracellular portion of a 7-TDGR in transfected host cells is greatly facilitated by producing the extracellular portion as a fusion with a membrane anchor portion. The extracellular and membrane anchor portions are preferably joined in or by a region having a protease cleavage site, allowing convenient release and purification of the extracellular portion of the receptor from other cellular components.

The invention is described in detail below with respect to the glycoprotein hormone receptors (McFarland, et al., 1989; Nagayama and Rapoport, 1992). It will be appreciated, however, that the invention encompasses analogous compositions and methods derived from or relating to other subclasses of the 7-transmembrane domain G-protein-coupled receptor superfamily. In particular, it is contemplated that this discovery is applicable to at least all 7-transmembrane domain G-protein-coupled receptors primarily responsive to peptides (Fong, et al., 1993) and/or glycoprotein hormones (Reichert, et al., 1991) as their primary specific ligands, as well as to 7-transmembrane domain G-protein-coupled receptors that serve to facilitate pathogen (e.g., viral) entry into cells (Feng, et al., 1996).

IV. Exemplary 7-TDGRs For Use With the Invention

A. Glycoprotein Hormone Receptors

The GhR receptors are members of the 7-transmembrane domain G-protein-coupled receptor superfamily (Reichert, et al., 1991). They can be divided into distinct "domains" based on the primary sequence and similarity to other 7 transmembrane G-protein-coupled receptors. The N-terminal, or extracellular, domain contains between about 330 and 420 amino acids and is primarily responsible for ligand binding. According to the present invention, truncated "receptors" containing only this extracellular domain retain ability to bind ligand and have been termed "soluble receptors" or "soluble glycoprotein hormone binding proteins" (sGhBPs).

The transmembrane domain, which includes the 7 transmembrane alpha-helices, typically spans about 280–290 amino acids. The C-terminal intracellular domain is generally between about 60 and 80 amino acids in length. The human FSH receptor (GenBank Accession numbers M65085, M95489) contains about 695 amino acids, with 366 comprising the extracellular domain (of which 17 amino acids comprise the signal sequence at the N-terminus). The human LH/CG receptor (GenBank Accession number M63108) contains about 699 amino acids, with 341 comprising the extracellular domain. The human TSH receptor (GenBank Accession numbers M31774 and M32215) contains about 764 amino acids, with about 410 comprising the extracellular domain.

The present invention is directed in one aspect to chimeric GhRs, where the receptor's extracellular domain or portion thereof is linked to any suitable transmembrane anchor via a sequence or moiety which allows the extracellular domain of the receptor to be cleaved from the transmembrane anchor. Specifically, the chimeric receptor is a chimeric polypeptide formed of a first segment that contains an N-terminal amino acid sequence of a glycoprotein hormone receptor polypeptide, a second segment that contains a membrane anchor polypeptide, and interposed between the first and second segments, a cleavable site such as a protease recognition site. The first segment is all or a part of the extracellular domain of a GhR, which contains between about 280 and 420 amino acid residues, depending on the type of receptor.

The second segment, containing a membrane anchor, is a sequence which is capable of assuming a transmembrane orientation when expressed in a host cell. In a trivial example, the second segment is simply the remainder of the receptor from which the first segment was obtained. In this embodiment, the chimeric polypeptide of the present invention is a GhR (e.g., FSHR) with a cleavage site located between the N-terminal extracellular domain and the transmembrane domain.

In other embodiments, the second segment is derived from a different protein having a transmembrane domain. For example, in embodiments described in the Examples below, the second segment is a transmembrane portion of a CD8 molecule. Transmembrane portions of other proteins may be used as well.

The cleavage site, located between the first and second segments, allows the release of "soluble receptors". In a general embodiment, the cleavage site is an amino acid sequence recognized by a selected protease (i.e., a protease recognition site). The selected protease preferably has an extended substrate recognition sequence which does not correspond to any other sequences present in the extracellular domain. Among the potentially-useful proteases are factor Xa, thrombin (Smith and Johnson, 1988; Gearing, et al., 1989), enterokinase, renin, and collagenase. An embodiment of the invention described in the Examples, below, incorporates a thrombin recognition sequence in the chimeric peptide.

A protease cleavage site in the present invention typically comprises a discrete sequence separating the first and second segments. However, it is contemplated that such a site may be created by altering the sequences in the region of the junction to correspond to a protease recognition site, e.g., engineering conservative substitutions into the amino acid sequences of the first and/or second segments in the region of the junction. In such an embodiment, the cleavage recognition sequence is not a separate fragment, but rather, is formed of portions of the first and second segments. Of course, combinations of the above may also be employed.

Chimeric receptors such as described above are encoded by chimeric nucleic acid molecules, which are formed of a 5' end segment that encodes the N-terminal amino acid sequence of a glycoprotein hormone receptor polypeptide, a 3' end segment that encodes a membrane anchor polypeptide, and interposed between (or formed from the adjacent portions of) the 5' end segment and 3' end segment, a segment encoding a cleavable site such as a protease recognition site. The chimeric nucleic acid molecules are preferably derived from human sequences, to minimize immunogenic responses if used in humans. The chimeric nucleic acid molecules may optionally also contain known sequences that improve the characteristics of the nucleic acid molecule or receptor it encodes, and/or facilitates the purification of the soluble receptor. For example, sequences encoding a tag (e.g., poly-histidine (His tag), M1 or HA) can be included, e.g., downstream of the signal peptide or upstream of the proteolytic cleavage site, so that the soluble binding proteins can be more easily purified using affinity methodologies (nickel column for His tag, monoclonal antibodies for M1 and HA).

The present invention also includes an expression vector suitable for use in a method of recombinantly producing a soluble receptor, or chimeric polypeptide, such as described above. The vector includes a polynucleotide containing an open reading frame that encodes the chimeric polypeptide described above, and regulatory sequences effective to express the open reading frame in a selected host cell. The regulatory sequences may include sequences useful for targeting or secretion of the chimeric polypeptide. Such sequences may be endogenous (such as the normally occurring GhR leader sequences) or heterologous (such as a secretory signal recognized in yeast, mammalian cell, insect cell, tissue culture or bacterial expression systems). In the expression vector, regulatory sequences may also include, 5' to said nucleic acid sequence, a promoter region and an ATG start codon in-frame with the chimeric polypeptide coding sequence, and 3' to said coding sequence, a translation termination signal followed by a transcription termination signal.

The construction of two exemplary expression vectors, pcDNA3LCD8 and pcDNA3FCD8, is described in Example 1. To make pcDNA3LCD8, the first segment, encoding the extracellular region of the LH receptor, and the second segment, encoding the transmembrane region through the cytoplasmic tail and 3' untranslated region of CD8, were cloned into the commercially-available mammalian expression vector pcDNA3 (Invitrogen Corp., San Diego, Calif.). Plasmid pcDNA3FCD8 was similarly constructed using the extracellular domain from the human FSH receptor and the CD8 cDNA. Example 5 describes the construction of a baculovirus expression vector.

Numerous vectors and their corresponding hosts are useful in the practice of this method of the invention, including, yeast, mammalian cell, insect cell, tissue culture, plant cell culture, transgenic organisms or bacterial expression systems. Eukaryotic expression systems are preferred, since they are typically capable of glycosylating the expressed protein.

The invention further includes a method of recombinantly producing the chimeric polypeptide described above, to generate cells expressing the chimeric polypeptide, which in turn may be incubated with an agent capable of cleaving the chimeric polypeptide at the cleavage site, to release the soluble receptor. The method includes the following steps. First, an expression vector containing an open reading frame (ORF) having a polynucleotide sequence which encodes the chimeric polypeptide (such as the vector described above) is introduced into suitable host cells. The vector is designed to express the ORF in the host cells. The vector may be introduced into the cells using any suitable transformation method, e.g., electroporation (Ausubel, et al., 1988).

Also included in the invention are host cells transformed with the constructs described herein. The host cells are typically selected based on the type of expression vector used (see above). The transformed host cells are cultured under conditions resulting in the expression of the ORF sequence. Following expression of the chimeric polypeptide on the surface of the cells (e.g., as described in Example 1), the extracellular domain, containing the soluble receptor, may be conveniently cleaved by incubating the cells in the presence of a protease which recognizes the protease recognition site incorporated into the construct.

Following cleavage from their membrane anchor, the soluble receptor molecules of the invention or conjugates thereof are typically purified or separated away from other cellular contaminants, e.g., as described in Example 5. The soluble receptor polypeptides may be further purified by standard known protein purification procedures, including differential precipitation, molecular sieve chromatography, ion-exchange chromatography, isoelectric focusing, gel electrophoresis and affinity chromatography. Protein preparations can also be concentrated by, for example, filtration (Amicon, Danvers, Mass.).

Example 3 describes such an application of the present invention. Here, plasmids pcDNA3LCD8 and pcDNA3FCD8 were modified to include a thrombin cleavage site between the truncated GhR portion and the transmembrane anchor portion of the expressed chimeric polypeptide. The modified vectors were used to transfect cells and express protein as described above. The cells were then treated with thrombin to release the truncated LH and FSH soluble receptors. The soluble receptors were analyzed using the binding assay described in Example 2 as well as cross-linking analysis and SDS PAGE. The results of these experiments indicate that the soluble receptors retain their ligand binding ability and are of the predicted size.

Alternatively, the expressed fusion proteins may be left on the host cells which expressed them, and the cells may be used for, e.g., binding assays. For instance, Example 2 describes the binding of labelled LH and FSH to cells transfected with the respective receptors. The results of these assays suggest that high levels of binding sites are localized on the plasma membrane approximately 8h after transfection.

In addition to glycoprotein hormone receptors, preferred embodiments of the invention include those derived from other receptors having a substantial extracellular domain, particularly those that distinguish between closely-related ligand molecules, e.g., the vasoactive intestinal polypeptide (VIP) family of receptors. Several exemplary receptors and ligands, amenable for use with specific embodiments of the present invention, are described below. The extracellular portions of these other receptors may then be employed and used as described herein (e.g., with respect to GhRs) for, e.g., derivation of soluble binding proteins for specific ligands, antibodies or viral proteins.

B. Calcitonin Receptor Family

Calcitonin is a peptide which inhibits bone resorption and thus leads to a reduction in plasma $[Ca^{++}]$. Calcitonin also enhances excretion of ions in the kidney, prevents absorption of ions in the intestine and inhibits secretion in endocrine cells, such as in the pancreas and pituitary. In the central nervous system (CNS), calcitonin has been reported to be analgesic and to suppress feeding and gastric acid secretion. In brain, the calcitonin gene transcript is alternatively spliced to produce an mRNA which encodes calcitonin-gene related peptide (CGRP) (Epand and Caulfield, 1990). CGRP is a potent vasoactive and cardiotonic peptide and stimulator of gastric acid secretion (Brain & Cambridge, 1996)

The calcitonin receptor (Lin, et al., 1991) is found predominantly on osteoclasts and on immortal cell lines derived from these cells. It is present in lower amounts in brain, e.g., hypothalamus and pituitary, and in peripheral tissues, e.g., testes, kidney, liver and lymphocytes. The receptor has also been described in lung and breast cancer cell lines. The sequence of the pig calcitonin receptor is available under GenBank accession number M74420. The first transmembrane domain begins at about amino acid number 148; accordingly, the extracellular domain includes amino acids 1—147.

Two subtypes of the CGRP receptor have been proposed, based on differences in potency of analogs and CGRP fragments (Dennis, et al., 1989a, 1989b). CGRP is a potent and long-acting vasodilator in the cerebral, coronary and peripheral vasculature (Brain and Cambridge, 1996; Feuerstein, et al., 1995). According to the present invention, soluble ligand-binding domains of the CGRP receptor can be used, e.g., to neutralize endogenous CGRP to treat vascular diseases, including migraine and vasospasm. CGRP antagonist have been also shown to improve insulin sensitivity in non-insulin dependent diabetes (Feuerstein, et al., 1995), since CGRP reduces the tissue glucose response to insulin. According to the present invention, the soluble ligand-binding domains of CGRP may be used to improve insulin sensitivity in non-insulin dependent diabetes.

C. Glucagon Receptor

Glucagon is required for control of blood glucose levels. The peptide stimulates glycogenolysis and gluconeogenesis in liver, producing glucose for release into the bloodstream. It also causes lipolysis in liver and fat cells. Its major actions are therefore opposite from those of insulin, and it has a major role in the pathogenesis of diabetes. Glucagon has also occasionally been used to increase force and rate of contraction during acute cardiac failure.

The sequence of glucagon is conserved across all mammalian species, and shares a limited sequence similarity with members of the VIP family (for example, 15 of the amino acids in glucagon are present in secretin)

The glucagon receptor (Jelinek, et al., 1993) is expressed predominantly in liver. It is also found in adipose tissue and in heart. The sequence of the rat glucagon receptor is available through GenBank at accession numbers L04796 and M96674. The first transmembrane domain begins at about amino acid number 144; accordingly, the extracellular domain includes amino acids 1—143.

There are at present no clinically useful antagonists for the glucagon receptor. According to the present invention, soluble ligand binding domains of the receptor, generated, e.g., as described herein, may be administered as functional antagonists for the glucagon receptor, by binding to and thereby decreasing the concentration of free glucagon.

Such glucagon antagonists could be used, for example, to lower blood glucose levels in type II diabetics (Vantine, et al., 1996).

D. Glucagon-Like Peptide 1 (GLP-1) Receptor

GLP-1 upregulates glucose-induced insulin secretion and suppresses stomach acid secretion (Goke, et al., 1991). Although derived from the same precursor as glucagon, GLP-1 has a distinct structure and is not active at the glucagon receptor. Non-insulin-dependent diabetes mellitus is associated with a reduced stimulatory effect of GLP-1 on glucose-induced insulin secretion.

The sequence of the rat GLP-1 receptor (Thorens, 1992) is available through GenBank at accession number M97797. The first transmembrane domain begins at about amino acid number 146; accordingly, the extracellular domain includes amino acids 1—145. The extracellular region of GLP-1 receptor has been shown to bind GLP-1 (Wilmen, et al., 1996). Further, it is recognized that GLP-1 is involved in the regulation of food consumption (Thiele, et al., 1997) and that central administration of GLP-1 inhibits food and water intake in rats (Tanchristensen, et al., 1996). According to the present invention, soluble ligand binding domains of the GLP-1 receptor may be used to treat patients with eating disorders such as anorexia nervosa.

E. Metabotropic Glutamate Receptor Family

Glutamate is the predominant excitatory neurotransmitter in the CNS, and is thought to have important roles in cognition, memory, neuronal plasticity, learning and some neurological disorders such as epilepsy, stroke and neurodegeneration (Schoepp and Conn, 1993). Its actions are mediated through two distinct classes of receptors, termed ionotropic and metabotropic receptors. Ionotropic receptors are glutamate-activated ion channels which mediate "fast" excitatory actions of glutamate.

Metabotropic glutamate receptors belong to the 7-transmembrane domain G-protein-coupled receptor family and exert their function through interactions with G-proteins. At least five such metabotropic glutamate receptors have been identified (Masu, et al., 1991; Tanabe, et al., 1992; Abe, et al., 1992; Takahashi, et al., 1993), and have a range of physiological effects, including increasing the membrane excitability of neurons by inhibiting $Ca^{2+}$ dependent $K^+$ conductances, inhibiting and potentiating excitatory transmission supported by ionotropic glutamate receptors, and inhibiting the afterhyperpolarization that follows bursts of actions potentials in the dentate gyrus and CA1 neurons in the hippocampus. They are also involved in long-term potentiation. A full understanding of their physiological roles, however, is hampered by the lack of selective agonists and antagonists.

Sequences of different glutamate receptors are available, e.g., from GenBank as accession numbers M61099 (Rat mGluR1), M92075 (Rat mGluR2), M92076 (Rat mGluR3), M92077 (Rat mGluR4), and D10891 (Rat mGluR5). The first transmembrane domain of mGluR1 begins at about amino acid number 593; accordingly, the extracellular domain includes amino acids 1—592 (although the first ~20 amino acids are thought to be a signal sequence). The first transmembrane domain of mGluR2 begins at about amino acid number 568; accordingly, the extracellular domain includes amino acids 1—567 (although the first ~18 amino acids are thought to be a signal sequence). The first transmembrane domain of mGluR3 begins at about amino acid number 577; accordingly, the extracellular domain includes amino acids 1—576 (although the first ~22 amino acids are thought to be a signal sequence). The first transmembrane domain of mGluR4 begins at about amino acid number 588; accordingly, the extracellular domain includes amino acids 1—587 (although the first ~32 amino acids are thought to be a signal sequence). The first transmembrane domain of mGluR5 begins at about amino acid number 579; accordingly, the extracellular domain includes amino acids 1—578 (although the first ~20 amino acids are thought to be a signal sequence).

According to the present invention, soluble ligand binding domains of the various glutamate receptors can be used, for example, in binding assays to screen for selective agonists and/or antagonists of the different receptors.

F. Parathyroid Hormone Receptor Family

Parathyroid hormone (PTH) is associated with calcium homeostasis within the body. It acts in combination with calcitonin and vitamin D (Epand and Caulfield, 1990; Muff, et al., 1992). PTH is released in direct response to hypocalcaemia, stimulating a rise in blood calcium. As such, its actions are opposite to those of calcitonin. PTH acts mainly in bone (osteoblasts) and kidney. In osteoblasts, PTH is thought to decrease matrix production and release cytokines involved in osteoclast recruitment and activation. In kidney, PTH decreases reabsorption of phosphate and increases reabsorption of calcium in renal tubules. It also stimulates increased production of 1,25 dihydroxyvitamin $D_3$, which results in increased absorption of calcium in the intestine.

The PTH receptor (Juppner, et al., 1991; Abou-Samra, et al., 1992) is found in bone and kidney, and, to a lesser extent, in blood vessels where it mediates vasodilation. The receptor is also activated by PTH-related peptide at concentrations similar to those required for PTH activation (subnanomolar range). The sequence of the PTH receptor is available, e.g., from GenBank as accession number M77184. The first transmembrane domain begins at about amino acid number 182; accordingly, the extracellular domain includes amino acids 1—181 (although the first ~22 amino acids are thought to be a signal sequence).

According to the present invention, soluble ligand binding domains of the PTH receptor can be used as functional antagonists of the PTH receptor. Such antagonists can be used, for example, to treat hyperparathyroidism and short-term hypercalcemic states. Specifically, in patients with uremic hyperparathyroidism associated with enlarged parathyroid gland and hyper-secretion of PTH (Indridason, et al., 1996), soluble PTH receptor extracellular region may be used to neutralize the action of endogenous PTH. The same binding protein may be used to neutralize ectopic production of PTH-related protein which is the common cause of hypercalcemia in patients with solid tumors such as squamous and renal carcinomas (Nielsen, et al., 1996).

G. VIP Receptor Family

Vasoactive intestinal peptide (VIP) is one of a family of structurally-related peptides sharing an overlapping profile of biological activities (Said and Mutt, 1988), including VIP, secretin, growth hormone releasing factor (GRF), pituitary adenyl cyclase activating polypeptide (PACAP), and peptide histidine methionamide (PHM). Although the peptides can generally activate receptors for the other related peptides, the affinity of the peptides for the related receptors is typically an order of magnitude or more lower than for their corresponding receptors.

VIP has a number of physiological actions. For example, in the periphery, it (i) induces relaxation in smooth muscle (e.g., blood vessels, intestine, and trachea), (ii) inhibits secretion in certain tissues (e.g., stomach) and stimulates secretion in others (e.g., pancreas, intestinal epithelium, and gall bladder), and (iii) modulates activity of cells in the immune system. In the CNS, VIP has a similarly wide range of excitatory and inhibitory activities.

Secretin stimulates secretion of ions and enzymes in the intestine and pancreas, but is present in relatively small amounts in certain areas of the brain, including the hypothalamus, brainstem and cerebral cortex. GRF is an important neuroendocrine agent that regulates the synthesis and release of growth hormone from the anterior pituitary. It is found primarily in the hypothalamus.

Exemplary receptors in this family are the VIP and secretin receptors. The VIP receptor is distributed throughout the periphery, gastrointestinal tract, the genitourinary system, other smooth muscles (e.g., trachea, blood vessels), and in secretory glands (e.g., pancreas, gall bladder). In the CNS, VIP receptors are present in high levels in the hippocampus, cerebral cortex, thalamus, and striatum.

The sequence of the VIP receptor (Ishihara, et al., 1992) is available, e.g., from GenBank as accession number M86835. The first transmembrane domain begins at about amino acid number 146; accordingly, the extracellular domain includes amino acids 1—145 (although the first 30 amino acids are thought to be a signal sequence).

The secretin receptor (Ishihara, et al., 1991) sequence is available from GenBank under accession number X59132. Its first transmembrane domain begins at about amino acid number 144; accordingly, the extracellular domain includes amino acids 1—143 (although the first ~22 amino acids are thought to be a signal sequence).

Since peptide antagonists of VIP have been shown to attenuate vagally induced tachycardia in experimental animals (Hill and Wallick, 1995), it is contemplated that soluble ligand binding regions derived from the VIP receptor and effective to neutralize endogenous VIP can be used as antagonist for vagally-induced tachycardia.

The human GRF receptor has been cloned (Mayo, 1992). The sequence can be found under GenBank Accession number L01406. The first 133 amino acids encode the extracellular region (including the signal peptide). An exemplary application of an anchored GRF receptor produced according to the present invention is a screen for the isolation of selective GRF receptor agonists and antagonists (see the screening section, below). A GRF agonist effective to stimulate pituitary release of GH would be particularly useful as a pharmaceutical for increasing muscle tone and general well-being in aging men.

V. Applications of Soluble Glycoprotein Hormone Receptors Produced According to the Invention.

A. Efficient Expression of Soluble Receptors

As detailed above, the present invention enables efficient production of recombinant glycoprotein hormone receptor extracellular domains. Previous attempts to produce such soluble receptors have resulted in the sequestration of the receptors inside the cells, necessitating cell-extraction prior to receptor purification, and/or self-aggregation of the receptors, necessitating harsh partial denaturation and refolding.

In contrast, methods of the present invention enable the production and isolation of large amounts of recombinant soluble receptor protein, which can be harvested and purified without solubilizing the host cells or resorting to unpredictable treatments to induce correct folding.

Following cleavage from their membrane anchor, the soluble receptor molecules of the invention or conjugates thereof are typically purified or separated away from other cellular contaminants, e.g., as described in Example 5. The soluble receptor polypeptides may be further purified by standard known protein purification procedures, including differential precipitation, molecular sieve chromatography, ion-exchange chromatography, isoelectric focusing, gel electrophoresis and affinity chromatography. Protein preparations can also be concentrated by, for example, filtration (Amicon, Danvers, Mass.).

B. Generation of anti-GhR Antibodies

Soluble ligand binding regions of GhRs produced according to the methods described herein may be used to generate antibodies against particular selected receptor ligand binding regions. Typically, to prepare antibodies, a host animal, such as a rabbit, is immunized with the purified antigen or fused protein antigen using known techniques (e.g., Harlow, et al., 1988). The host serum or plasma is collected following an appropriate time interval, and this serum is tested for antibodies specific against the antigen. The gamma globulin fraction or the IgG antibodies of immunized animals can be obtained, for example, by use of saturated ammonium sulfate or DEAE Sephadex, or other techniques known to those skilled in the art for producing polyclonal antibodies.

Alternatively, a purified sGhBP, particularly a soluble antigenic domain of a GhR, may be used for producing monoclonal antibodies. Here the spleen or lymphocytes from an immunized animal are removed and immortalized or used to prepare hybridomas by methods known to those skilled in the art (e.g., Harlow, et al.) . Antibodies secreted by the immortalized cells are screened to determine the clones that secrete antibodies of the desired specificity, for example, using Western blot analysis according to known methods (e.g., Ausubel, et al., 1988).

C. Contraceptive Applications

Purified soluble LH and FSH binding proteins (i.e., soluble receptors that retain ligand-binding activity) may be used in a number of applications, particularly in fertility and contraceptive applications. Since soluble LH, FSH and CG ligand binding domains produced according to the methods of the present invention are capable of binding to their respective agonist hormones, they can be administered therapeutically to an individual to preferentially neutralize the action of individual gonadotropins by decreasing the availability of the selected gonadotropins to bind to receptors present on the surfaces of target cells.

FSH is released from the pituitary in response to gonadotropin-releasing hormone and CG and from the placenta during pregnancy. In males, FSH is important for spermatogenesis. In females, FSH promotes development of the follicles and regulates secretion of oestrogens. It is contemplated that administration of extracellular ligand binding regions of FSH receptors to males and females will result in infertility, and can be used as a reversible method of contraception.

Contraceptive effect may also be achieved by administering the ligand binding region of the LH receptor to block the action of LH or CG.

In this context, therefore, the invention also includes methods of contraception. In one embodiment, the method includes administering a pharmaceutically-effective dose of an extracellular ligand binding region (ELBR) of a human FSH receptor. In another embodiment, the method includes administering a pharmaceutically-effective dose of an ELBR of a human LH receptor.

D. Polycystic Ovarian Disease

Polycystic ovarian (PCO) disease (Petersdorf, et al., 1983) is characterized by high LH levels and low FSH levels. PCO patients are usually treated with GnRH analogs that suppress both LH and FSH, followed by FSH administration. According to the present invention, PCO disease can be treated by administering the ligand binding domains of the LH/CG receptor acts to decrease the amount of LH available to bind to LH/CG receptors on ovarian thecal cells, thereby decreasing the amount of androgen synthesized and allowing endogenous FSH to promote follicle development.

Similar treatments can be applied to, e.g., patients with precocious puberty and/or ovarian hyper-stimulation syndrome (Fauser, 1996). Ovarian hyper-stimulation syndrome is detrimental to patients undergoing gonadotropin therapy due to excess LH/FSH secretion by the pituitary. In addition to the withdrawal of gonadotropins, the administration of LH and FSH binding proteins could neutralize circulating gonadotropins.

E. Treatment of Steroid-Dependent Tumors, Including Breast Cancer, Prostate Cancer and Thyroid Cancer Ligand binding domains of the FSH and LH receptors (e.g., FBP and LBP) may be used to treat gonadotropin-dependent, steroid-dependent or TSH-dependent tumors, such as breast cancer, prostate cancer, and thyroid cancer. Such tumors typically require the presence of gonadotropins or TSH to grow or survive. Depletion of circulating gonadotropin or TSH by sGhRs of the invention may be used to inhibit the growth of such tumors relative to the growth of similar but untreated tumors. The GhRs may also be used to titer circulating gonadrotropin and/or TSH levels in patients with gonadotropin and/or TSH-producing tumor(s).

Breast cancer is a leading cause of death in women between the ages of 35 and 45. Although many factors affect the likelihood that a particular woman will get breast cancer, the presence or absence of the estrogen receptor (ER) protein is generally considered to be particularly important in determining the prognosis of the disease. Specifically, women who have high ER levels have a more favorable prognosis than women whose ER levels are intermediate or low relative to normal. In view of this finding, breast cancer patients are sometimes provided with estrogen analogues in order to abolish the action of estrogen or estrogen precursors. In more extreme cases, adrenalectomy and/or hyphosectomy may be performed.

According to the present invention, by administering an extracellular ligand binding domain of an FSH receptor to a breast cancer patient, it is possible to bind the patient's FSH molecules, and thereby prevent or attenuate the ability of such FSH molecules to induce ovarian cells to produce estrogen.

Ligand binding domains of the FSH and LH receptors (e.g., FBP and LBP) may also be used to treat steroid-dependent prostate cancer. Like breast cancer in women, prostate cancer is a leading cause of cancer deaths in men. The disease is typically treated by surgical removal of the prostate gland, chemotherapy, and radiation therapy. Growth of the prostate gland is dependent upon testicular androgens (principally testosterone). Accordingly, the therapies listed above are typically accompanied by therapies designed to decrease the level of testosterone, such as castration or anti-androgen therapy.

According to the present invention, a lowering of testosterone level can also be achieved by administering an extracellular ligand binding domain of the LH receptor. The principal action of LH in males is to induce Leydig cells to produce testosterone. Consequently, by providing an individual with the soluble ligand binding domain of the LH/CG receptor, the amount of LH in the serum which is available to induce testosterone biosynthesis can be decreased. Administration of the soluble receptor(s) will thus decrease testosterone synthesis, resulting in a decreased rate of growth of the prostate gland.

Such therapy may be used for inhibiting tumor growth, causing tumor regression, as well as for decreasing bone pain (which is typically a symptom in most patients exhibiting an advanced stage of disease).

F. Applications of sGhBPs with Altered Ligand Binding Affinities

Soluble glycoprotein hormone binding proteins (sGhBPs) of the present invention having altered binding affinity for their respective glycoprotein hormones may be used in a number of applications, some of which are detailed below.

For example, sGhBPs having decreased binding affinity for their respective glycoprotein hormones may be used as "co-hormones" to extend the circulating half life of the endogenous glycoprotein hormones. An exemplary application of this approach is in the treatment of hypogonadotropic hypogonadism. Here, one can mutate the ligand binding region of an sGhBPs so that it has low affinity to its respective ligand. The mutant sGhBPs may then be co-administered with specific glycoprotein hormones to decrease the metabolism of the hormones and prolong their in vivo half-life and potency.

In a related application, aspects of which are embodied in some of the therapies (e.g., anti-cancer therapies) discussed above, sGhBPs can be used as "decoys" for the endogenous GhRs. Such "decoy" GhBPs may be designed to bind their respective Gh as well as or better than the endogenous GhR, binding up free Gh.

"Non-binding" soluble GhRs, such as soluble TSH receptors having little or no affinity for TSH, may be used, for example, in the treatment of autoimmune disease. For example, stimulatory and inhibitory antibodies against the TSH receptor cause thyroid dysfunctions (Nagayama and Rapoport, 1992; Tomer and Davies, 1993). Grave's disease is a form hyperthyroidism caused by stimulatory auto-immune antibodies to the extracellular region of the TSH receptor, whereas Hashimoto disease is caused by inhibitory auto-immune antibodies (Magner, et al., 1990). Similarly, premature ovarian failure has been associated with circulating antibodies against FSH receptors (Chiauzzi, et al., 1982; Dias, et al., 1982).

According to the present invention, autoimmune diseases in which an endogenous extracellular ligand binding domain of a 7-TDGR is targeted by the patient's own antibodies, such as Grave's disease and premature ovarian failure, may be treated by administration of soluble ligand binding regions, such as those derived from TSH or FSH receptors, that have been mutated in a way to disrupt glycoprotein hormone binding without substantially affecting the ability of the soluble ligand binding regions to bind the antibodies. These mutated sGhRs will then bind up the autoimmune antibodies without substantially interfering with GhR signalling.

G. Screen for Gh Peptide Mimetics

Methods and compositions of the present invention may be used in screens to identify compounds or peptides that bind to 7-transmembrane domain G-protein-coupled receptors. Such compounds or peptides may be mimetics, agonists or antagonists of the endogenous ligands. For example, such screens may be used to identify compounds or peptides that mimic the action of FSH, LH, or TSH on their respective receptors.

In one embodiment, the screen is a method of identifying a compound capable of affecting binding of a ligand (e.g., peptide ligand) to its corresponding 7-transmembrane domain G-protein-coupled receptor. Exemplary receptors amenable to the screening method have been identified above. The method includes contacting an anchored receptor construct derived from the corresponding receptor with the ligand, in the presence and absence of a test compound, measuring the effect of the test compound on the extent of binding between the ligand and anchored receptor, and identifying the compound as effective to alter binding of the ligand to its corresponding 7-transmembrane domain G-protein-coupled receptor if the measured effect of the compound on the extent of binding is above a threshold level.

The above method may be used to screen libraries of compounds in multi-well plates (e.g., 96-well plates), with a different test compound in each well. In particular, the method may be employed with combinatorial libraries. A variety of combinatorial libraries of random-sequence oligonucleotides, polypeptides, or synthetic oligomers have been proposed (e.g., Houghten, 1985, 1994; Houghten, et al., 1986, 1991, 1992). A number of small-molecule libraries have also been developed (e.g., Bunin, et al., 1994; Virgilio and Ellman, 1994).

Combinatorial libraries of oligomers may be formed by a variety of solution-phase or solid-phase methods in which mixtures of different subunits are added stepwise to growing oligomers or parent compound, until a desired oligomer size is reached (typically hexapeptide or heptapeptide). A library of increasing complexity can be formed in this manner, for example, by pooling multiple choices of reagents with each additional subunit step (Houghten, et al., 1991).

Alternatively, the library may be formed by solid-phase synthetic methods in which beads containing different-sequence oligomers that form the library are alternately mixed and separated, with one of a selected number of subunits being added to each group of separated beads at each step. The identity of library compounds with desired effects on the binding of the ligand to the anchored receptor can be determined by conventional means, such as iterative synthesis methods in which sublibraries containing known residues in one subunit position only are identified as containing active compounds.

In another embodiment, the screen is used to directly isolate a compound having a high affinity for the anchored receptor. For example, in one specific embodiment, the screen is carried out using a phage display library of combinatorial peptides (Cwirla, et al., 1990; Devlin, et al., 1990; Scott and Smith, 1990), where the expressed peptides are displayed as fusions to phage coat proteins. Affinity purification of the population of phage particles on the target protein is used to recover peptides with binding affinity.

As applied to the present case, a selected soluble glycoprotein hormone receptor is expressed as a fusion in selected host cells, e.g., as described above. The soluble receptor is then cleaved from its membrane anchor and attached inside a well of an assay plate via, e.g., an antibody that does not interfere with agonist binding. Alternatively, the cells are plated into assay wells and immobilized therein via antibodies (such as are used in "panning purifications") or other means, and the anchored receptors are left on the cells which expressed them.

The immobilized receptors or cells are then used to screen a phage display library as described (Wrighton, et al., 1996), and phage which bind to the receptors are isolated by affinity purification of the receptors (Wrighton, et al., 1996). If cells are used in the screen, the selected receptors are typically separated from the cells by cleavage with the appropriate protease prior to affinity purification.

It should be noted that the inclusion of a proteolytic cleavage site allows discrimination between specific and non-specific interactions of candidate molecules, because only compounds which bind specifically will be cleaved (along with the extracellular domain) following thrombin treatment. This approach can substantially enhance the selectivity of the screening procedure. It is particularly amenable for use with anchored glutamate receptors, described above.

A variety of different compounds may be screened using methods of the present invention. They include peptides, macromolecules, small molecules, chemical and/or biological mixtures, and fungal, bacterial, or algal extracts. Such compounds, or molecules, may be either biological, synthetic organic, or even inorganic compounds, and may be obtained from a number of sources, including pharmaceutical companies and specialty suppliers of libraries (e.g., combinatorial libraries) of compounds.

In cases where an identified active compound is a peptide, the peptide may be utilized to design a peptoid mimetic and aid in the discovery of orally-active small molecule mimetics. Alternatively, the peptides themselves may be used as therapeutics. Further, the structure of a bioactive polypeptide may be determined using, for example, NMR, and may be used to select the types of small molecules screened.

It will be understood that after identifying certain test compounds as potential receptor agonists or antagonists agents, the practitioner of the screening assay will typically continue to test the efficacy and specificity of the selected compounds both in vitro and in vivo. Whether for subsequent in vivo testing, or for administration to an animal as an approved drug, agents identified in the screening assay can be formulated in pharmaceutical preparations for in vivo administration to an animal, preferably a human.

In this context, the screening method includes, in one embodiment, the further step of preparing a pharmaceutical preparation of a compound identified as effective to alter binding of a ligand to its anchored receptor. The compounds selected in the screening assay, or a pharmaceutically acceptable salt thereof, may be formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the compound, its use in the pharmaceutical preparation of the invention is contemplated.

Suitable vehicles and their formulation inclusive of other proteins are described, for example, in Gennaro, 1990. These vehicles include injectable "deposit formulations". Based on the above, such pharmaceutical formulations include, although not exclusively, solutions or freeze-dried powders of the compound in association with one or more pharmaceutically acceptable vehicles or diluents, and contained in buffered media at a suitable pH and isosmotic with physiological fluids. In a preferred embodiment, the compound can be disposed in a sterile preparation for topical and/or systemic administration. In the case of freeze-dried preparations, supporting excipients such as, but not exclusively, mannitol or glycine may be used and appropriate buffered solutions of the desired volume will be provided so as to obtain adequate isotonic buffered solutions of the desired pH. Similar solutions may also be used for the pharmaceutical compositions in isotonic solutions of the desired volume and include, but not exclusively, the use of buffered saline solutions with phosphate or citrate at suitable concentrations so as to obtain at all times isotonic pharmaceutical preparations of the desired pH (for example, neutral pH).

H. Advantages

The soluble ligand binding regions derived from glycoprotein hormone receptors have a number of advantages over other types of receptor antagonists. For example, such SLBRs are designed to bind specific hormones and are unlikely to show agonistic activity, in direct contrast to hormone antagonists that interact with target organ receptors and usually exhibit agonistic activity at high concentrations. Accordingly, they can be used to selectively and differentially affect signalling pathways mediated by closely-related molecules (e.g., LH and FSH). Furthermore, receptor antagonists do not have to be delivered to the target tissues and, due to their similarity to wild type receptors, have low antigenicity.

VI. Administration of Soluble Receptors of the Invention

The present invention includes methods of administering therapeutic or prophylactic compositions containing an effective amount of at least one of the soluble receptors or active fragments thereof, typically suspended in or conjugated to a suitable vehicle or carrier. When provided prophylactically, the compound(s) are provided in advance of any symptom of a disease, or sign of a condition (e.g., contraceptive applications). Therapeutic application, in contrast, is provided after the onset of a symptom of an existing disease, to treat the disease. The therapeutic administration of the compound(s) serves to attenuate the symptoms or such disease or condition.

A. Preparation of Therapeutic/Prophylactic Compositions

The soluble receptors, therapeutically-active fragments or conjugates thereof may be formulated into physiologically acceptable carriers and sterile filtered for therapeutic use. A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The molecules may be formulated and administered according to known methods for the preparation and administration of proteinaceous pharmaceutical compositions (see, e.g., Banga, 1995). For example, the molecules or their functional derivatives may be combined with a pharmaceutically acceptable carrier, excipient, and/or other vehicle. Suitable vehicles and their formulation are described, for example, in Gennaro (1990) and Banga (1995), and include nonionic detergents such as Tween 20 or 80, salts, buffers, and other excipients. The therapeutic compositions may be stored as aqueous solutions or lyophilized.

Control release preparations may be formed using polymers to complex or absorb the molecules of the present invention. Such polymers may be used, for example, to control the rate of release or the duration of action of the therapeutic compounds of the invention. Examples of suitable polymers include polyesters, polyamino acids, hydrogels, polylactic acid and ethylene vinylacetate copolymers. Alternatively or in addition, the therapeutic compounds of the invention can be entrapped in microcapsules prepared, for example, by coacervation techniques or by interfacial polymerization, for example, hydroxymethylcellulose or gelatine- microcapsules and poly (methylmethacylate) microcapsules, respectively, or in colloidal drug delivery systems, for example, suspension in a lipid or phospholipid, in a liposomal suspension, in an aqueous emulsion (microemulsions or macroemulsions), with albumin microspheres, nanoparticles, and nanocapsules. These and other approaches are disclosed in, e.g., Gennaro, 1990.

Therapeutic and/or prophylactic compositions of the invention may be administered by subcutaneous, intramuscular, intravenous, or intracerebrospinal injection, intrapulmonary or intranasal aerosols, dermal patches, intravesicular infusion, or the like. When administering by injection, the administration may be by continuous infusion, or by single or multiple boluses.

B. Dosage

The dosage of therapeutic compound administered is determined in accord with clinical practice, and will vary depending upon such factors as the patient's age, height, weight, sex, previous medical history, and general medical condition. Typically, it is desirable to provide the recipient with an initial dose of from about 300 µg/kg to about 10 mg/kg (body weight of patient), daily or several (e.g., 3) times per week, although a lower or higher dosage may be administered.

The dose is determined in part based on the pharmacokinetics of clearance of the administered receptor or SBP using standard pharmacokinetics principles known in the art. Methods for preparing such dosages are known or will be apparent to those skilled in the art; for example, see Gennaro (1990).

The concentration of the molecules of the present invention in therapeutic formulations is not critical, but typically ranges from about 1 µg/ml to about 20 mg/ml. In Example 5, for instance, the administered concentration was about 30 µg/ml.

The following examples illustrate but in no way are intended to limit the present invention.

MATERIALS AND METHODS

Unless otherwise indicated, restriction enzymes and DNA modifying enzymes were obtained from New England Biolabs (Beverly, Mass.) or Boehringer Mannheim (Indianapolis, Ind.), and other chemicals were purchased from Sigma (St. Louis, Mont.) or United States Biochemical (Cleveland, Ohio).

| Phosphate-buffered saline (PBS) |
| --- |
| 10x stock solution, 1 liter: |
| 80 g NaCl<br>2 g KCl<br>11.5 g $Na_2HPO_4$-$7H_2O$<br>2 g $KH_2PO_4$ |
| Working solution, pH 7.3: |
| 137 mM NaCl<br>2.7 mM KCl<br>4.3 mM $Na_2HPO_4$-$7H_2O$<br>1.4 mM $KH_2PO_4$ |

B. Radiolabeling Binding Assays

Human choriogonadotropin (CR129) and human FSH (NIDDK-I-1) were obtained from the National Hormone and Pituitary Agency (Baltimore, Md.) and iodinated using the lactoperoxidase method (Thorell and Johansson, 1971). The specific activities of the tracers were ~100,000 cpm/ng for $I^{125}$- FSH and ~50,000 cpm/ng for $I^{125}$-hCG. Transiently transfected cells were incubated with radioligands in 300 µl of PBS containing 0.1% bovine serum albumin (BSA) at 23° C. for 18h. Non-specific binding was determined by adding excess unlabeled hormones (100 IU hCG/tube or 4 IU FSH/tube).

Following estimation of optimal binding conditions, radio-ligand receptor assays for cells transfected with FtCD8 and LtCD8 were performed at 22° C. for 5 h and 2 h, respectively. After incubation, cells were washed twice followed by centrifugation and determination of radioactivity using a gamma-counter.

EXAMPLE 1

Construction and Expression of Plasmid Constructs

Plasmid pcDNA3LCD8, encoding a fusion between the extracellular domain of the human LH receptor (Jia, et al., 1991) and the single transmembrane domain of CD8, was constructed using the polymerase chain reaction (PCR; Mullis, 1987; Mullis, et al., 1987) as follows. An EcoRV-XbaI fragment, encoding the CD8 transmembrane region (amino acid 162 to the C-terminus, (Littman, et al., 1985)), was isolated from the plasmid pSK-ATE-CD8 (Chen, et al., 1994; provided by Dr. Shaun Coughlin, UCSF, San Francisco, Calif.). The EcoRV-XbaI fragment was ligated to another polynucleotide fragment encoding the extracellular region of the LH receptor (LH receptor amino acid 1–355, (Jia, et al., 1991)) through a thrombin cleavage site (amino acids 36 to 66 of the thrombin receptor (Vu, et al., 1991; Chen, et al., 1994)) and subcloned into the expression vector pcDNA3 (Invitrogen Corp., San Diego, Calif.). The resulting junction between LH receptor and thrombin receptor encoded . . . NPCED/ATLDP . . . (SEQ ID NO:1), whereas the junction between thrombin receptor and CD8 encoded the sequence . . . NESGL/IYIWA . . . (SEQ ID NO:2). The fusion polypeptide encoded by this construct was termed LtCD8.

Plasmid pcDNA3FCD8, encoding a fusion of the extracellular domain from the human FSH receptor and the transmembrane domain of CD8, was constructed by fusing the extracellular domain of human FSH receptor (amino acids 1–358, (Tilly, et al., 1992)) to the transmembrane and cytoplasmic region of CD8 through the thrombin receptor sequence as described above. The resulting junction between FSH receptor and the thrombin receptor sequence contained the sequence . . . NPCED/ATLDP . . . (SEQ ID NO:3), whereas the junction between thrombin receptor and CD8 was the same as that in LtCD8.

Plasmid pcDNA3TCD8, encoding a fusion of the extracellular domain from the human TSH receptor (amino acid 1 to 410; Nagayama and Rapoport, 1992) with the transmembrane domain of CD8 through the thrombin receptor sequence, was constructed as described above. The junction between the TSH receptor and the thrombin receptor sequence contained the sequence . . . NPCED/ATLDP . . . (SEQ ID NO:4). The resulting construct was termed TtCD8.

For expression of wild type and chimeric receptors in human embryonic kidney 293 cells, receptor cDNAs were subcloned into pcDNA3 (Invitrogen, San Diego, Calif.). Cell culture and transient expression were performed as previously described (Kudo, et al., 1996). Briefly, 293 cells were cultured in the DMEM/F12 medium supplemented with 10% serum and antibiotics. After replacement of the medium by DMEM supplemented with 10% serum and antibiotics, 293 cells were transfected using 10 µg expression vector containing wild type and chimeric receptor cDNAs by the calcium phosphate precipitation method (Tilly, et al., 1992).

EXAMPLE 2

Ligand Binding to Transfected Cells

Human embryonic kidney 293 cells transfected with wild-type or chimeric receptors as described above were assayed for their ability to bind the ligand of the receptors they were transfected with. The cells were incubated with labeled ligands (FSH or hCG) and equilibrium binding constants were determined using Scatchard plot analysis (Scatchard, 1949). Radiolabeling and binding was done as described above.

Figure 2B:
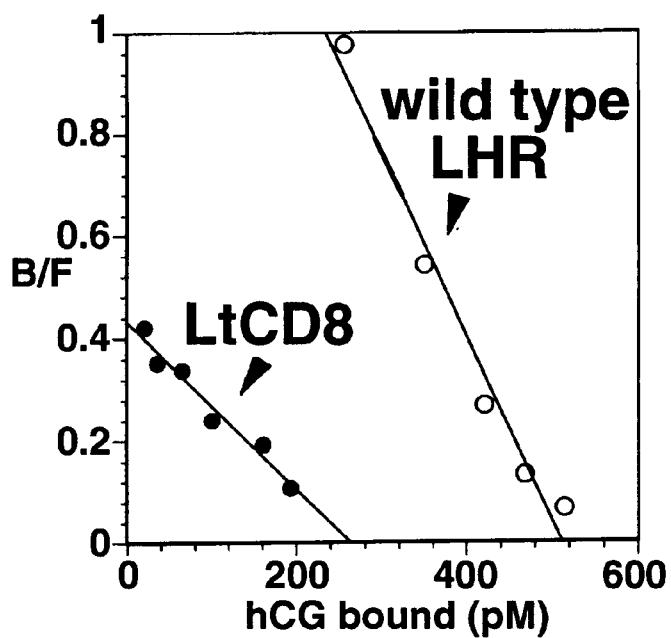
FIG. 2B is a plot of the binding kinetics of wild type LH receptor and LtCD8.

The results are show in FIGS. 2A and 2B as binding kinetics of wild type FSH receptor and FtCD8 (FIG. 2A), and wild type LH receptor and LtCD8 (FIG. 2B). Kd values are as follows: FtCD8: 0.31 nM; wild type FSH receptor: 1.03 nM; LtCD8: 0.61 nM; wild type LH receptor: 0.28 nM. For anchored FtCD8, the binding affinity to radiolabeled FSH was 3-fold higher than that of the wild type receptor, with the number of receptors per cell estimated at ~17,000 for FtCD8 and ~30,000 for FSHR. Anchored LtCD8 showed binding affinity comparable to that of the wild type receptor.

These results demonstrate that the extracellular regions of gonadotropin receptors can be expressed on the cell surface of transfected cells at levels comparable to those of the wild type receptors independent of the seven-transmembrane region, and retain high affinity binding to specific ligands.

The cells were also incubated with appropriate labeled ligands at 4° C., 22° C. and 3720 C. for times ranging from 0.5h to 48h to assess optimal ligand binding condition for each receptor. Results of these experiments suggested that high levels of binding sites are localized on the plasma membrane 8h after transfection.

EXAMPLE 3

Cleavage and Analysis of Solubilized Ligand Binding Regions

The ligand binding regions of the anchored receptors described above were solubilized by treating transfected 293 cells expressing wild-type or anchored (FtCD8 or LtCD8) receptor with 10 IU/ml α-thrombin to release receptor extracellular regions. Conditioned medium (10× concentrated using Centricon 30, Amicon, Bedford, Mass.)) was then incubated with labeled ligands at 23° C. for 5 hours (medium from FtCD8-transfected cells) or at 4° C. for 16–18 hours (medium from LtCD8-transfected cells) followed by cross-linking with disuccinimidyl suberate (2 mM) for 1h. The crosslinking reaction was terminated by the addition of 3.6 mM Tris-HCl pH 7.4.

Thrombin treatment was omitted for control groups whereas some groups were incubated with excess non-labeled ligands to demonstrate binding specificity. After the addition of Laemmeli buffer without reducing reagents, cross-linked complexes formed between labeled hormones and the solubilized receptor fragments were characterized following fractionation using polyacrylamide (10w) gel electrophoresis (PAGE).

Figure 2C:
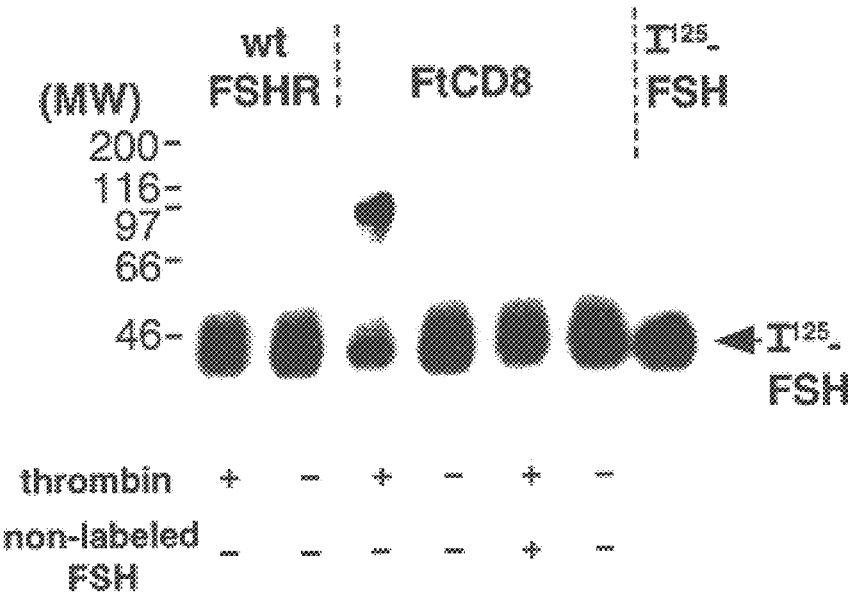
FIG. 2C is a computer-generated image of a gel showing cross-linking of labeled ligands to solubilized extracellular domain of the FSHR/CD8 fusion (FtCD8) following thrombin cleavage of the anchored receptor.
Figure 2D:
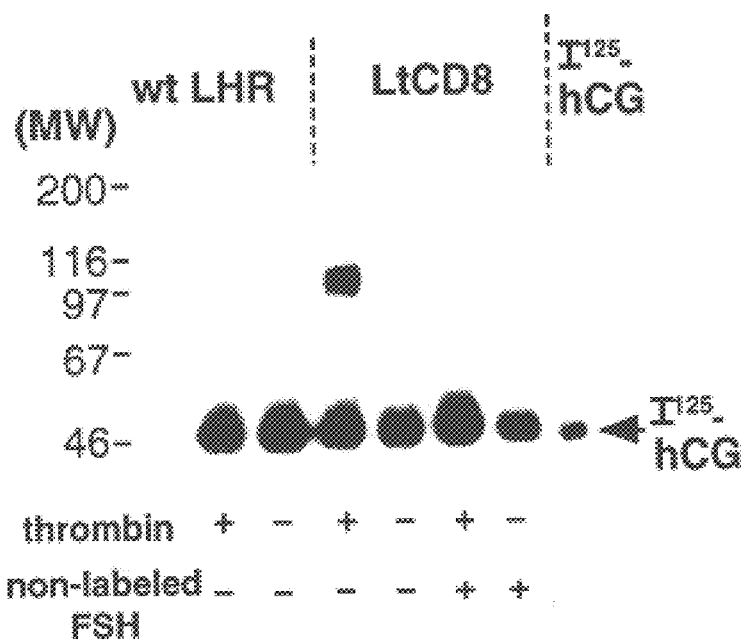
FIG. 2D is a computer-generated image of a gel showing cross-linking of labeled ligands to solubilized extracellular domain of the LHR/CD8 fusion (LtCD8) following thrombin cleavage of the anchored receptor.

The results are illustrated in FIGS. 2C and 2D. Abbreviations are wt FSHR: wild type FSH receptor; wt LHR: wild type LH receptor. Migration patterns of molecular weight markers and labeled ligands are shown. Labeled FSH migrated as a 45 Kd band after gel electrophoresis whereas the conditioned media from FtCD8-expressing cells pretreated with thrombin showed a higher molecular weight band (90 Kd), indicating the formation of complexes between labeled FSH and the extracellular region of FSH receptor (FIG. 2C). Complex formation was inhibited by the inclusion of excess non-labeled FSH and was not found in cells expressing wild type receptors or without thrombin pretreatment. Likewise, thrombin pretreatment allowed the formation of a 105 Kd complex between labeled hCG and the extracellular region of LH receptor (FIG. 2D).

These results demonstrate that functional ligand binding domains of gonadotropin receptors can be generated using the anchored receptor approach, and that the soluble receptors retain their ligand binding ability and are of the predicted size. The soluble receptor fragments were named FBP (FSH binding protein) and LBP (LH/hCG-binding protein), respectively.

EXAMPLE 4

Inhibition of Gonadotropin Actions In Vitro

A. Competition Binding Assays

Binding assays were conducted to determine whether solubilized ligand binding regions of FSH and LH receptors block gonadotropin actions in vitro. In a radioligand binding assay, 293 cells expressing wild type human FSH or LH receptors were incubated with labeled FSH or hCG, respectively, in the presence or absence of increasing concentrations of solubilized extracellular regions of FSH receptor (FBP) and LH receptor (LBP). The amount of labelled FSH that remained bound to the cells was then determined.

Figure 3A:
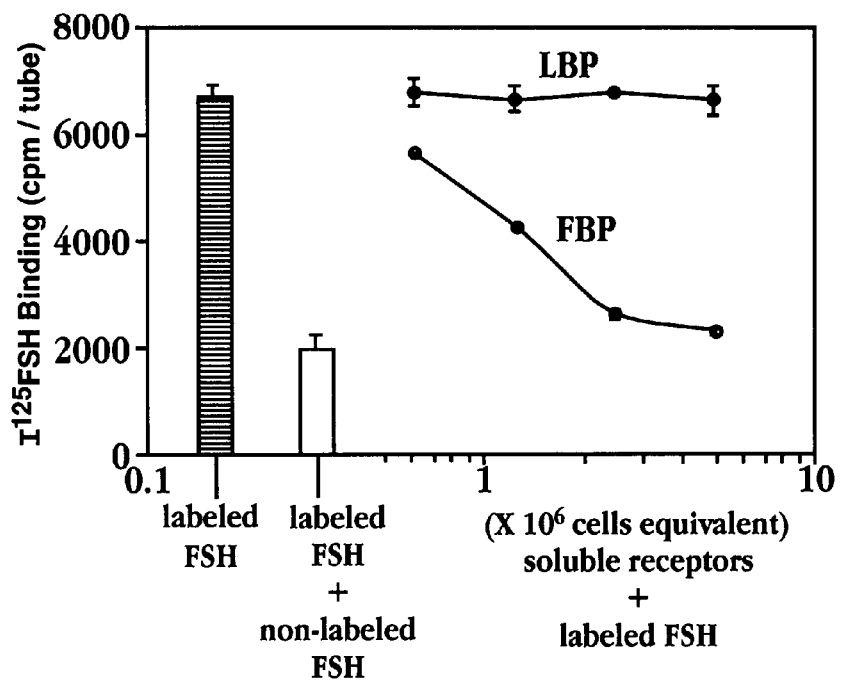
FIG. 3A is a graph showing competition of labeled FSH binding to FSH receptors by (i) FSH binding protein (FBP; the soluble ligand-binding extracellular domain of the FSH receptor), and (ii) LH/hCG-binding protein (LBP; the soluble, ligand-binding extracellular domain of the LH receptor).
Figure 3B:
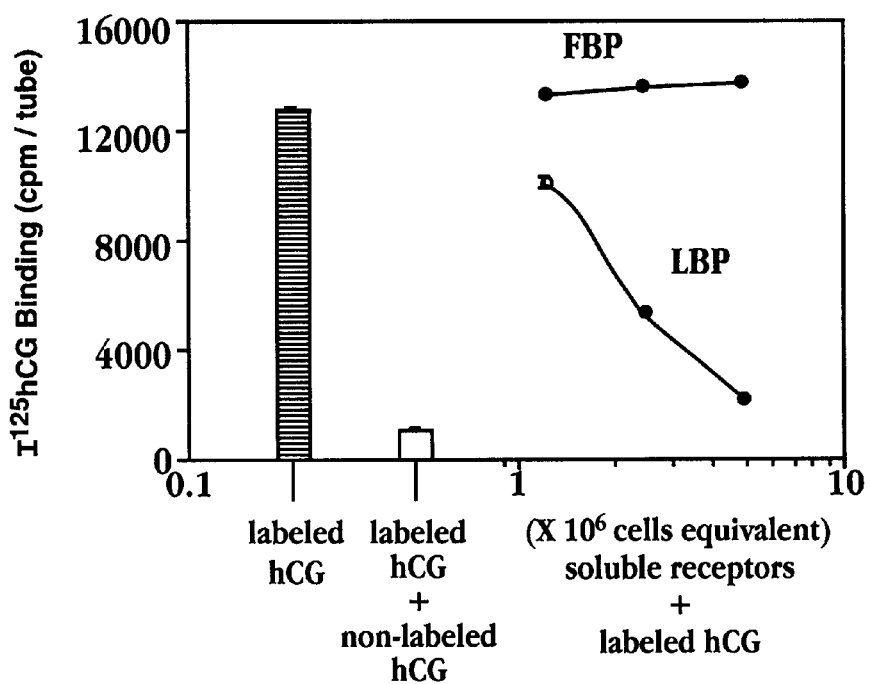
FIG. 3B is a graph showing competition of labeled hCG binding to LH receptors by FBP and LBP.

The results are shown in FIGS. 3A and 3B. As can be appreciated from FIG. 3A, addition of FBP prevented binding of labeled FSH to the wild type receptors in a dose-dependent manner, reaching a level comparable to non-specific binding. In contrast, inclusion of LBP was ineffective. The results show that solubilized extracellular regions of the FSH receptor (FBP) compete labeled FSH off the wild-type FSH receptors. Similarly, binding of labelled hCG to 293 cells expressing wild type human LH receptors was competed in a dose-dependent manner by LBP but not by FBP (FIG. 3B).

The results show that FBP and LBP specifically prevented the binding of FSH and LH, respectively, to their respective wild-type receptors.

B. cAMP Production

Additional experiments evaluated the ability of solubilized ligand binding regions to interfere with signal transduction induced by gonadotropins. 293 cells expressing wild type human FSH or LH receptors were incubated DMEM/F12, 0.1% BSA, with increasing concentrations of FSH or hCG in the presence or absence of FBP or LBP ($10^7$ cells equivalent/well) for 3h at 37° C. to stimulate cAMP production. Levels of cAMP were then determined by radioimmunoassay (Davoren and Hsueh, 1985). Concentration of binding proteins was determined based on their ability to inhibit the binding of respective labeled ligands to wild type receptors.

Figure 3C:
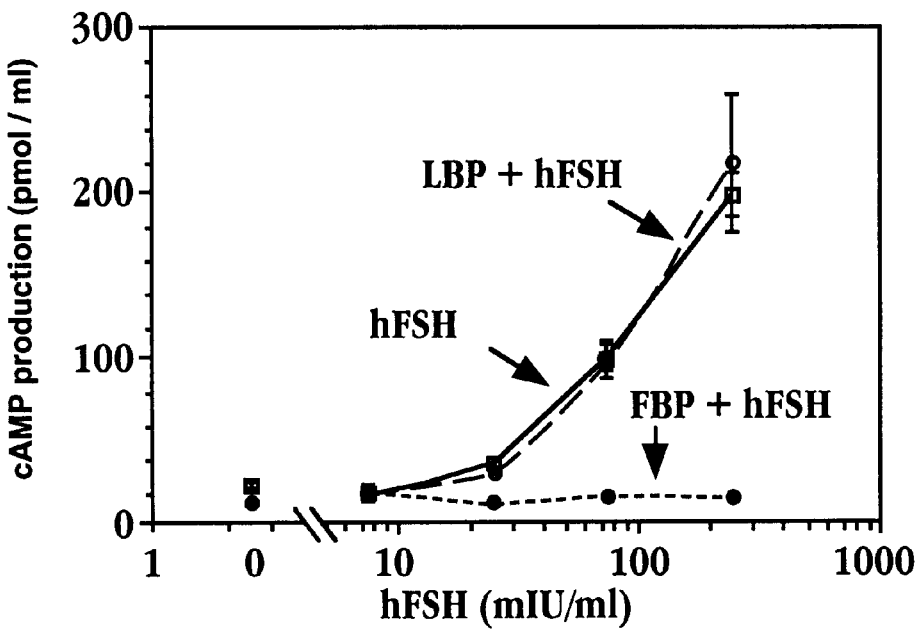
FIG. 3C is a plot showing antagonism of FSH stimulation of cAMP production by FBP but not LBP.
Figure 3D:
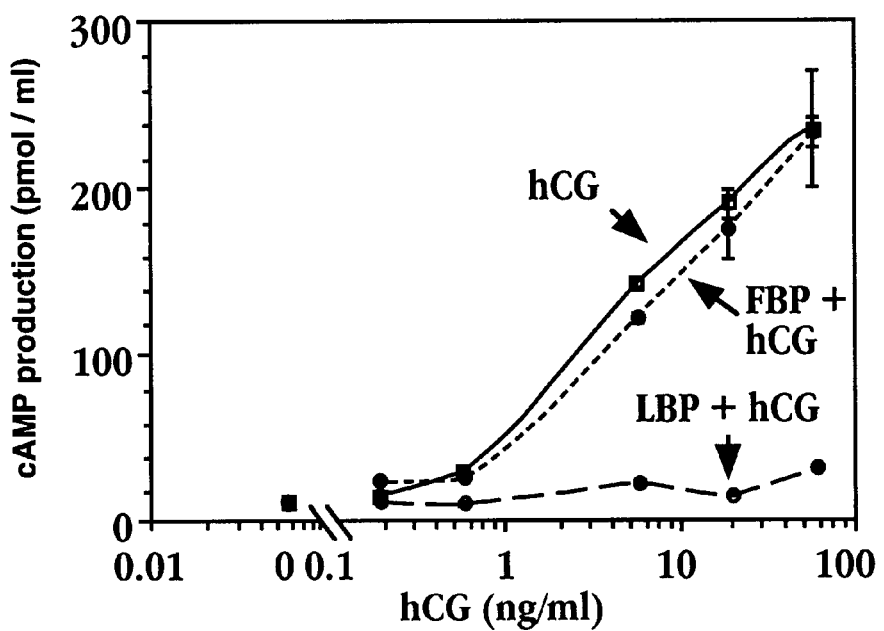
FIG. 3D is a plot showing antagonism of hCG stimulation of cAMP production by LBP but not FBP.

As shown in FIG. 3C, addition of FBP completely blocked cAMP production induced by FSH in FSH receptor-expressing cells, whereas LBP was ineffective. Results from experiments incubating cells expressing human LH receptors with hCG with or without LBP or FBP are shown in FIG. 3D. Addition of LBP inhibited cAMP stimulation by hCG in LH receptor-expressing cells, whereas FBP was ineffective.

A similar approach was used to evaluate the ability of solubilized TSH receptor fragments to interfere with cAMP production induced by human recombinant TSH (Genzyme, Cambridge, Mass.) in 293 cells transiently expressing human TSH receptors. Extracellular region of human TSH receptor, named as TSH binding protein (TBP) was generated using the same anchored receptor approach followed by thrombin treatment.

Figure 3E:
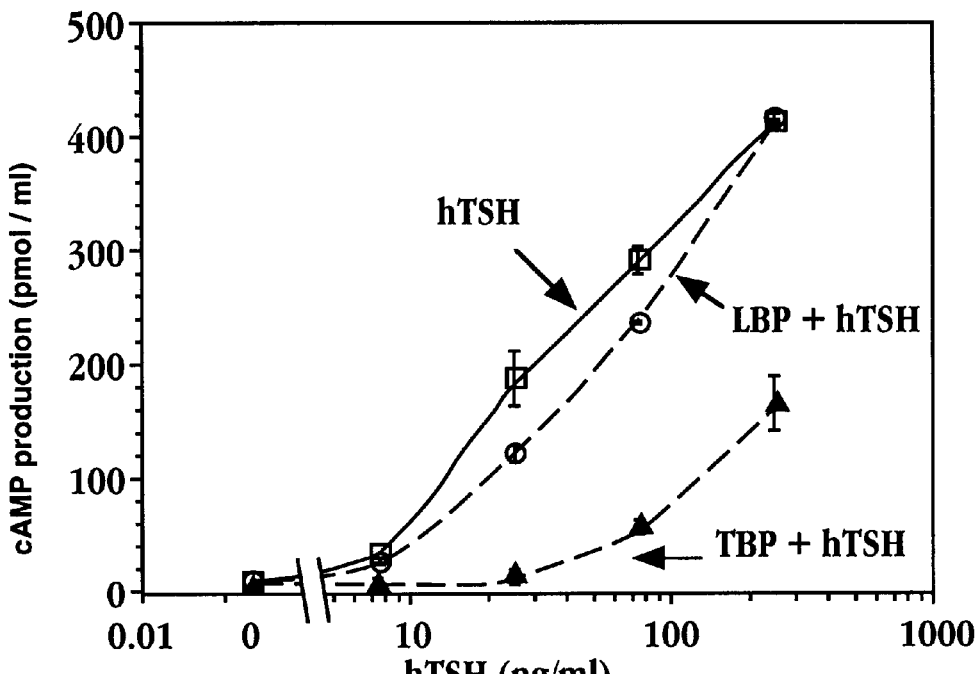
FIG. 3E is a plot showing antagonism of TSH stimulation of cAMP production by TBP but not LBP.
Figure 3F:
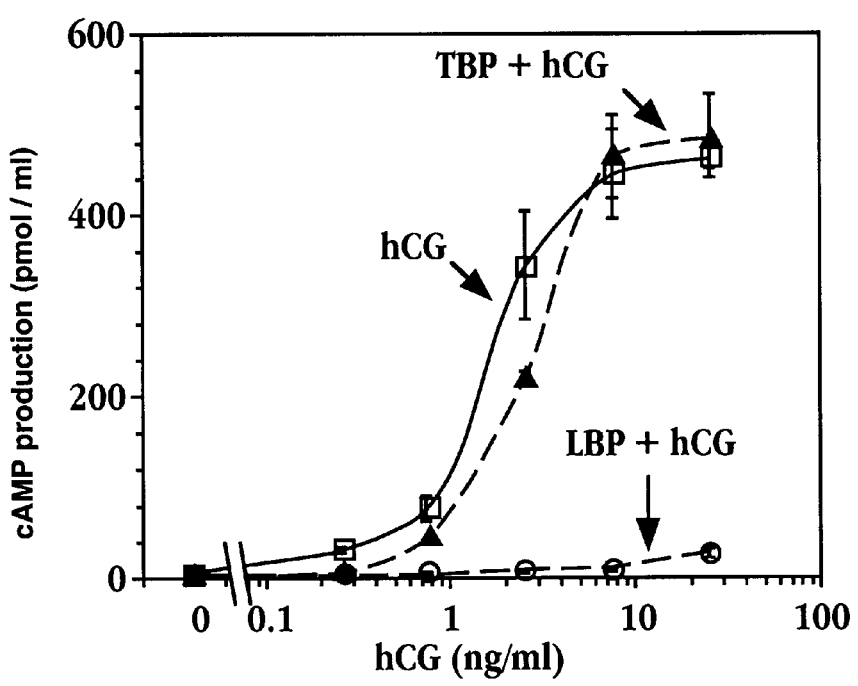
FIG. 3F is a plot showing antagonism of hCG stimulation of cAMP production by LBP but not TBP.

FIG. 3E shows that addition of TBP blocked cAMP production induced by TSH in a concentration-dependent manner in TSH receptor-expressing cells, whereas LBP was ineffective. FIG. 3F shows results of experiments incubating cells expressing human LH receptors with hCG with or without LBP or TBP. Addition of LBP inhibited cAMP stimulation by hCG in LH receptor-expressing cells, whereas TBP was ineffective.

The results summarized above demonstrate that the gonadotropin hormone binding proteins described herein (FBP, LBP and TBP) are capable of selective inhibition or blockage of gonadotropin and TSH -induced signal transduction in vitro.

EXAMPLE 5

Inhibition of Gonadotropin Actions In Vivo

A. Expression of FBP in Baculovirus

To test if FBP could be used as a functional antagonist in vivo, FtCD8 cDNA was subcloned into "pFAST BAC" vector and recombinant baculovirus was prepared using the "BAC-TO-BAC" baculovirus expression system (GIBCO-BRL, Gaithersburg, Md.) according to the protocol provided by the manufacturer. Recombinant baculovirus encoding FtCD8 was prepared using the manufacturer's instructions, and SF9 cells ($3\times10^6$ /ml) in SF900II medium containing 5% serum were infected with the recombinant viruses. After 72h culture at 27° C. in media containing 5% serum and thrombin (10 IU/ml), the cells were centrifuged to remove cell debris. The conditioned media were concentrated 30 times using DIAFLO ultrafiltration membrane XM50 (Amicon) and filtered with 0.2 $\mu$m filters (UNIFLO, Schleicher and Schuell, Keene, N.H.).

FBP produced by FtCD8-expressing insect cells was assayed for its ability to inhibit binding of labeled FSH to wild type FSH receptors in vitro as described above. The results were essentially identical to those obtained using the transfected 293 cells.

B. In vivo Induction of Testis Cell Apoptosis Following FBP Administration

Immature male rats (21 days of age, weighing between about 45 and 50 g) were injected subcutaneously (s.c.) every 6h for a period of 2 days with 1 ml conditioned media of SF9 cells ($10^8$ cells equivalent/injection) containing solubilized FSH receptor fragments prepared as described above. The concentration of soluble receptor protein in the injection volume was between about 30 and 100 $\mu$g/ml. The effective dose administered every 6 hours was therefore between about 6 and 20 mg/kg.

Two days after the initial injection, the testis were weighed and testis cell apoptosis was quantitated using a 3' end-labeling method (Tapanainen, et al., 1993). The effects of FBP were also assayed using in situ analysis of specific cell types undergoing apoptosis with the "APOTAG" kit (Oncor, Gaithersburg, Md.) as previously described (Billig, et al., 1995).

Some animals were treated with a potent gonadotropin releasing hormone (GnRH) antagonist (Org30850: Acetyl- D-parachloro-Phe (AcDpCl-Phe), D-parachloro-Phe (DpCl-Phe), D-Bal, DLys, DAla-amide; (AcDpCl)Phe1 - (DpCl) Phe2 - D-Bal3 - DLys6 -DAla10(amide) (SEQ ID NO:5; D refers to D (not L) amino acids); 50 μg/rat, FIG. 5C (ANT); Decker, et al., 1992) to suppress pituitary release of LH and FSH (Decker, et al., 1992) whereas others were treated with conditioned media of SF9 cells infected with wild type baculovirus. In situ analysis of specific cell types undergoing apoptosis was performed using Apotag kit (Oncor, Gaithersburg, MD) as previously described (Billig, et al., 1995). Animal care was in accordance with institutional guidelines.

Figure 4:
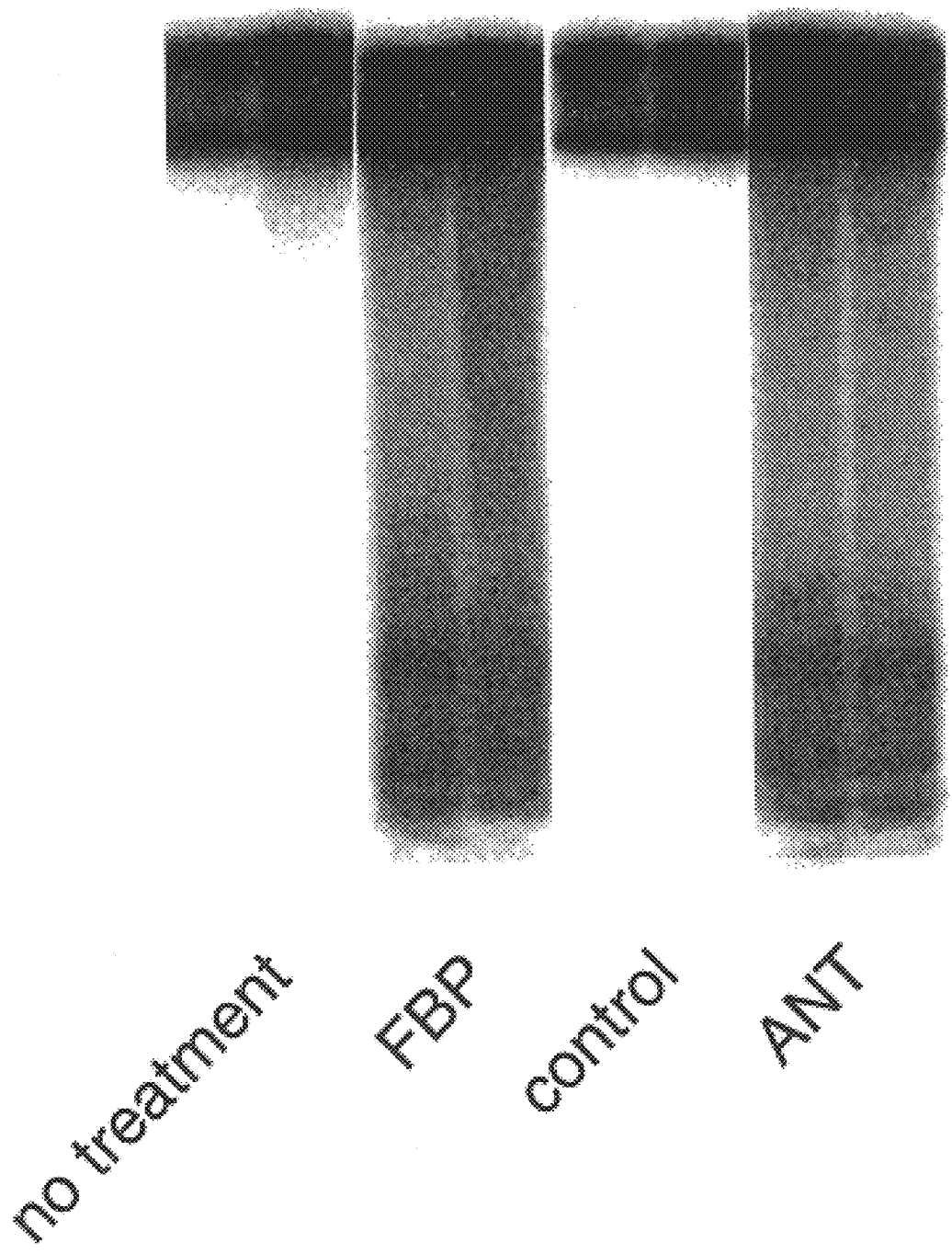
FIG. 4 is a computer-generated image of a gel showing the pattern of DNA fragmentation in a rat testis cell apoptosis assay under the indicated conditions.

Analysis of testis DNA fragmentation using a 3' end-labeling method followed by gel electrophoresis indicated major increases in testis cell apoptosis in the FBP-treated group, as evidenced by the appearance of internucleosomal DNA fragmentation (FIG. 4).

Figure 5A:
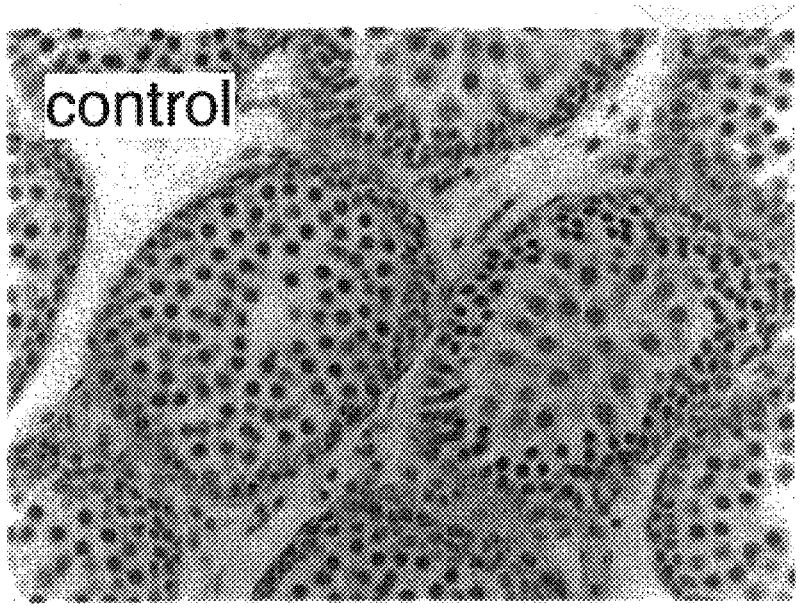
FIGS. 5A, 5B and 5C are computer-generated images showing in situ analysis of DNA fragmentation in control (FIG. 5A), FBP-treated (FIG. 5B) and Org30850treated (FIG. 5C) rat testis cells. Bar length: 25 μm.
Figure 5B:
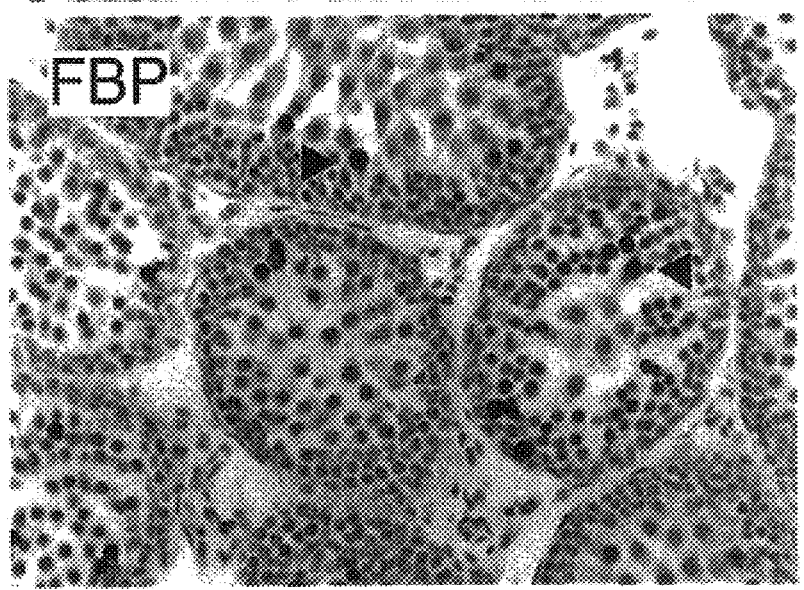
Figure 5C:
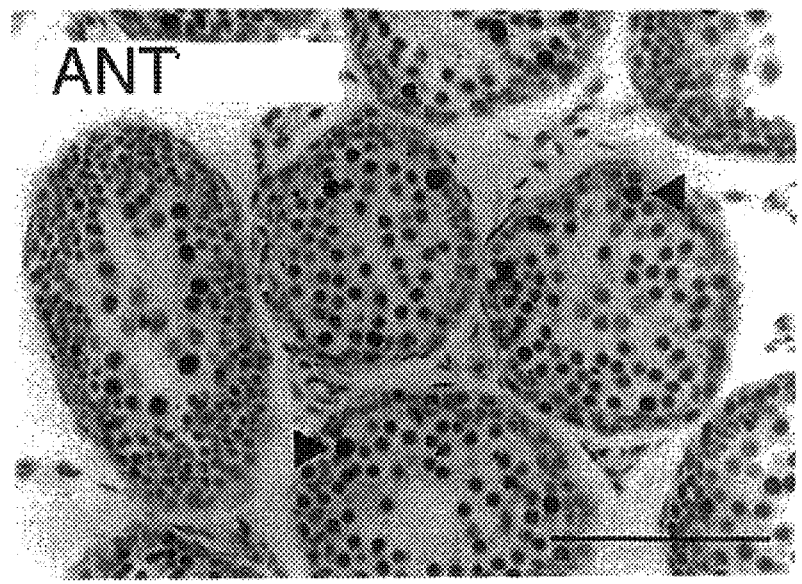

The results of the in situ analysis, illustrated in FIGS. 5A–C, show the effect of the treatment on testis cells. As can be appreciated from the figure, treatment with FBP for 2 days (FIG. 5B) induced major increases in DNA fragmentation. FBP treatment also attenuated testis growth by 33% (untreated: 192±28 mg; FBP-treated: 128±30 mg; n=14). Comparable decreases in testis weight (140±18 mg) and increases in apoptotic DNA fragmentation were found in rats treated with a GnRH antagonist (ANT; FIG. 5C) to suppress both LH and FSH secretion. In contrast, no retardation of testis growth (201±26 mg) or alteration of testis cell apoptosis were seen in rats treated with conditioned media of insect cells transfected with the wild type baculovirus (control; FIG. 5A).

These above results demonstrate that FBP is capable of neutralizing the action of endogenous FSH, which is essential for testis germ cell survival (Tapanainen, et al., 1993).

While the invention has been described with reference to specific methods and embodiments, it is appreciated that various modifications and changes may be made without departing from the invention.

It is claimed:

1. A nucleic acid encoding a chimeric polypeptide, comprising
   the first extracellular domain of a G-protein coupled receptor, wherein said first extracellular domain defines the ligand binding domain of said G-protein coupled receptor,
   a membrane anchor polypeptide joined at its amino terminus to the carboxyl terminus of said first extracellular domain, wherein said membrane anchor polypeptide is not naturally found in a G-protein coupled receptor, and
   a protease recognition site interposed between said first extracelluar domain and said membrane anchor polypeptide, wherein said protease recognition site is not present in said first extracelluar domain.

2. The nucleic acid of claim 1, wherein said protease recognition site is a thrombin recognition site.

3. The nucleic acid of claim 1, wherein said G-protein coupled receptor is a luteinizing hormone receptor.

4. The nucleic acid of claim 1, wherein said G-protein coupled receptor is a follicle stimulating hormone receptor.

5. The nucleic acid of claim 1, wherein said G-protein coupled receptor is a thyroid stimulating hormone receptor.

6. The nucleic acid of claim 1, wherein said membrane anchor polypeptide is the transmembrane portion of a CD8 molecule.

7. An expression vector comprising
   (a) the nucleic acid of claim 1; and
   (b) regulatory sequences effective to express said nucleic acid in a host cell.

8. The vector of claim 7, wherein the protease recognition site is a thrombin recognition site.

9. The vector of claim 7, wherein the membrane anchor polypeptide is the transmembrane portion of a CD8 molecule.

10. The vector of claim 7, wherein the G-protein coupled receptor is selected from the group consisting of a luteinizing hormone receptor, a follicle stimulating hormone receptor, a thyroid stimulating hormone receptor, a calcitonin receptor, a glucagon receptor, a glucagon-like peptide 1 receptor, a metabotropic glutamate receptor, a parathyroid hormone receptor, a vasoactive intestinal peptide receptor, a secretin receptor, and a growth hormone releasing factor receptor.

11. A method of recombinantly producing a chimeric polypeptide containing the first extracellular domain of a G-protein coupled receptor, wherein said first extracellular domain defines the ligand binding domain of said G-protein coupled receptor, comprising
    introducing into selected host cells, an expression vector of claim 7, where the regulatory sequences of the vector are effective to express said nucleic acid in said host cells, and
    culturing said host cells under conditions resulting in the expression of the nucleic acid.

12. The method of claim 11, which further includes incubating said host cells in the presence of a protease which recognizes said protease recognition site, to cleave said first extracellular domain from the remainder of said chimeric protein. molecule.

13. A host cell transfected with a vector of claim 7.

14. The nucleic acid of claim 1, wherein said G-protein coupled receptor is a calcitonin receptor.

15. The nucleic acid of claim 1, wherein said G-protein coupled receptor is a glucagon receptor.

16. The nucleic acid of claim 1, wherein said G-protein coupled receptor is a glucagon-like peptide 1 (GLP-1) receptor.

17. The nucleic acid of claim 1, wherein said G-protein coupled receptor is a metabotropic glutamate receptor.

18. The nucleic acid of claim 1, wherein said G-protein coupled receptor is a parathyroid hormone (PTH) receptor.

19. The nucleic acid of claim 1, wherein said G-protein coupled receptor is a vasoactive intestinal peptide (VIP) receptor.

20. The nucleic acid of claim 1, wherein said G-protein coupled receptor is a secretin receptor.

21. The nucleic acid of claim 1, wherein said G-protein coupled receptor is a growth hormone releasing factor (GRF) receptor.

22. The nucleic acid of claim 1, wherein said G-protein coupled receptor is a human G-protein coupled receptor.

23. A chimeric polypeptide comprising
    the first extracellular domain of a G-protein coupled receptor, wherein said first extracellular domain defines the ligand binding domain of said G-protein coupled receptor,
    a membrane anchor polypeptide joined at its amino terminus to the carboxyl terminus of said first extracellular domain, wherein said membrane anchor polypeptide is not naturally found in a G-protein coupled receptor, and a protease recognition site interposed between said first extracelluar domain and said membrane anchor polypeptide, wherein said protease recognition site is not present in said first extracelluar domain.

24. The polypeptide of claim 3, wherein said protease recognition site is a thrombin recognition site.

25. The polypeptide of claim 23, wherein said G-protein coupled receptor is a luteinizing hormone receptor.

26. The polypeptide of claim 23, wherein said G-protein coupled receptor is a follicle stimulating hormone receptor.

27. The polypeptide of claim 23, wherein said G-protein coupled receptor is a thyroid stimulating hormone receptor.

28. The polypeptide of claim 23, wherein said membrane anchor polypeptide is the transmembrane portion of a CD8 molecule.

29. The polypeptide of claim 23, wherein said G-protein coupled receptor is a calcitonin receptor.

30. The polypeptide of claim 23, wherein said G-protein coupled receptor is a glucagon receptor.

31. The polypeptide of claim 23, wherein said G-protein coupled receptor is a glucagon-like peptide 1 (GLP-1) receptor.

32. The polypeptide of claim 23, wherein said G-protein coupled receptor is a metabotropic glutamate receptor.

33. The polypeptide of claim 23, wherein said G-protein coupled receptor is a parathyroid hormone (PTH) receptor.

34. The polypeptide of claim 23, wherein said G-protein coupled receptor is a vasoactive intestinal peptide (VIP) receptor.

35. The polypeptide of claim 23, wherein said G-protein-coupled receptor is a secretin receptor.

36. The polypeptide of claim 23, wherein said G-protein coupled receptor is a growth hormone releasing factor (GRF) receptor.

37. The polypeptide of claim 23, wherein said G-protein coupled receptor is a human G-protein coupled receptor.

* * * * *